(12) United States Patent
Fish

(10) Patent No.: US 11,395,726 B2
(45) Date of Patent: Jul. 26, 2022

(54) CONDUIT VASCULAR IMPLANT SEALING DEVICE FOR REDUCING ENDOLEAKS

(71) Applicant: Incubar, LLC, Louisville, CO (US)

(72) Inventor: R. David Fish, Houston, TX (US)

(73) Assignee: INCUBAR LLC, Louisville, CO (US)

( * ) Notice: Subject to any disclaimer, the term of this patent is extended or adjusted under 35 U.S.C. 154(b) by 269 days.

(21) Appl. No.: 16/128,047

(22) Filed: Sep. 11, 2018

(65) Prior Publication Data
US 2019/0076233 A1  Mar. 14, 2019

Related U.S. Application Data

(60) Provisional application No. 62/556,612, filed on Sep. 11, 2017.

(51) Int. Cl.
| | | |
|---|---|---|
| A61F 2/07 | (2013.01) | |
| A61F 2/90 | (2013.01) | |
| A61B 17/12 | (2006.01) | |
| A61B 17/00 | (2006.01) | |

(52) U.S. Cl.
CPC ........... *A61F 2/07* (2013.01); *A61B 17/12113* (2013.01); *A61B 2017/00867* (2013.01); *A61F 2/90* (2013.01); *A61F 2002/075* (2013.01); *A61F 2002/077* (2013.01); *A61F 2250/0018* (2013.01); *A61F 2250/0069* (2013.01)

(58) Field of Classification Search
CPC ..................................... A61F 2/07; A61F 2/90
See application file for complete search history.

(56) References Cited

U.S. PATENT DOCUMENTS

| | | | |
|---|---|---|---|
| 3,014,024 A | 12/1961 | Lieberman et al. | |
| 3,029,819 A | 4/1962 | Edward | |
| 3,105,492 A | 10/1963 | Jeckel | |
| 3,320,972 A | 5/1967 | High et al. | |

(Continued)

FOREIGN PATENT DOCUMENTS

| | | |
|---|---|---|
| EP | 1603493 | 12/2005 |
| EP | 2000115 | 5/2011 |

(Continued)

OTHER PUBLICATIONS

International Search Report and Written Opinion dated Jan. 2, 2019 in Application No. PCT/US2018/050440.

(Continued)

*Primary Examiner* — Matthew W Schall
(74) *Attorney, Agent, or Firm* — Fox Rothschild LLP

(57) ABSTRACT

A sealing device for use as a vascular implant including a frame, the frame having an inflow edge and an outflow edge relative to axial blood flow within a vessel, wherein at least a partial axial extent of the frame is configured to decrease in axial length when expanded from a radially compressed configuration to a radially expanded configuration. The sealing device also includes a membrane layer coupled to a radially outward surface of the at least partial axial extent of the frame between the inflow edge and the outflow edge of the frame, wherein the membrane layer is coupled to the frame at one or more axially spaced connection points such that at least a portion of the membrane layer projects radially outward relative to the frame when the frame is in the radially-expanded configuration.

27 Claims, 14 Drawing Sheets

(56) References Cited

U.S. PATENT DOCUMENTS

| | | |
|---|---|---|
| 3,409,914 A | 11/1968 | Jones |
| 3,548,417 A | 12/1970 | Kischer et al. |
| 3,562,820 A | 2/1971 | Braun |
| 3,588,920 A | 6/1971 | Wesolowski |
| 3,671,979 A | 6/1972 | Mouloupoulos |
| 3,709,175 A | 1/1973 | Edwards et al. |
| 3,878,565 A | 4/1975 | Sauvage |
| 3,945,052 A | 3/1976 | Liebig |
| 3,966,401 A | 6/1976 | Hancock et al. |
| 3,983,581 A | 10/1976 | Angell et al. |
| 3,986,828 A | 10/1976 | Hoffman, Jr. et al. |
| 4,011,947 A | 3/1977 | Sawyer |
| 4,035,849 A | 7/1977 | Angell et al. |
| 4,055,861 A | 11/1977 | Carpentier et al. |
| 4,056,854 A | 11/1977 | Boretos et al. |
| 4,060,081 A | 11/1977 | Yannas et al. |
| 4,082,507 A | 4/1978 | Sawyer |
| 4,084,268 A | 4/1978 | Ionescu et al. |
| 4,106,129 A | 8/1978 | Carpentier et al. |
| 4,164,045 A | 8/1979 | Bokros et al. |
| 4,172,295 A | 10/1979 | Batten |
| 4,218,782 A | 8/1980 | Rygg |
| 4,222,126 A | 9/1980 | Boretos et al. |
| 4,233,493 A | 11/1980 | Nath |
| 4,265,694 A | 5/1981 | Boretos et al. |
| 4,291,420 A | 9/1981 | Reul |
| 4,340,977 A | 7/1982 | Brownlee et al. |
| 4,350,492 A | 9/1982 | Wright et al. |
| 4,364,127 A | 12/1982 | Pierce et al. |
| 4,388,735 A | 6/1983 | Ionescu et al. |
| 4,423,525 A | 1/1984 | Vallana et al. |
| 4,441,216 A | 4/1984 | Ionescu et al. |
| 4,456,589 A | 6/1984 | Holman et al. |
| 4,473,423 A | 9/1984 | Kolff |
| 4,477,930 A | 10/1984 | Totten et al. |
| 4,490,859 A | 1/1985 | Black et al. |
| 4,517,687 A | 5/1985 | Liebig et al. |
| 4,545,082 A | 10/1985 | Hood |
| 4,597,762 A | 7/1986 | Walter et al. |
| 4,600,533 A | 7/1986 | Chu |
| 4,631,052 A | 12/1986 | Kensey |
| 4,657,133 A | 4/1987 | Komatsu et al. |
| 4,666,442 A | 5/1987 | Arru et al. |
| 4,728,328 A | 3/1988 | Hughes et al. |
| 4,743,231 A | 5/1988 | Kay et al. |
| 4,759,758 A | 7/1988 | Gabbay |
| 4,798,611 A | 1/1989 | Freeman, Jr. |
| 4,801,299 A | 1/1989 | Brendel et al. |
| 4,870,966 A | 10/1989 | Dellon et al. |
| 4,883,458 A | 11/1989 | Shiber |
| 4,892,539 A | 1/1990 | Koch |
| 4,966,604 A | 10/1990 | Reiss |
| 4,976,733 A | 12/1990 | Girardot |
| 4,979,939 A | 12/1990 | Shiber |
| 5,006,104 A | 4/1991 | Smith et al. |
| 5,007,896 A | 4/1991 | Shiber |
| 5,011,488 A | 4/1991 | Ginsburg |
| 5,026,366 A | 6/1991 | Leckrone |
| 5,032,128 A | 7/1991 | Alonso |
| 5,047,041 A | 9/1991 | Samuels |
| 5,047,050 A | 9/1991 | Arpesani |
| 5,052,771 A | 10/1991 | Williams et al. |
| 5,061,277 A | 10/1991 | Carpentier et al. |
| 5,080,660 A | 1/1992 | Buelna |
| 5,139,515 A | 8/1992 | Robicsek |
| 5,163,955 A | 11/1992 | Love et al. |
| 5,171,273 A | 12/1992 | Silver et al. |
| 5,226,889 A | 7/1993 | Sheiban |
| 5,261,878 A | 11/1993 | Galindo |
| 5,282,847 A | 2/1994 | Trescony et al. |
| 5,326,370 A | 7/1994 | Love et al. |
| 5,326,371 A | 7/1994 | Love et al. |
| 5,332,402 A | 7/1994 | Teitelbaum |
| 5,336,616 A | 8/1994 | Livesey et al. |
| 5,360,443 A | 11/1994 | Barone et al. |
| 5,374,539 A | 12/1994 | Nimni et al. |
| 5,376,110 A | 12/1994 | Tu et al. |
| 5,383,927 A | 1/1995 | De Goicoechea et al. |
| 5,411,552 A | 5/1995 | Andersen et al. |
| 5,413,601 A | 5/1995 | Keshelava |
| 5,449,384 A | 9/1995 | Johnson |
| 5,476,506 A | 12/1995 | Lunn |
| 5,480,424 A | 1/1996 | Cox |
| 5,484,444 A | 1/1996 | Braunschweiler et al. |
| 5,489,297 A | 2/1996 | Duran |
| 5,500,015 A | 3/1996 | Deac |
| 5,509,930 A | 4/1996 | Love |
| 5,522,879 A | 6/1996 | Scopelianos |
| 5,522,881 A | 6/1996 | Lentz |
| 5,545,215 A | 8/1996 | Duran |
| 5,549,664 A | 8/1996 | Hirata et al. |
| 5,549,666 A | 8/1996 | Hata et al. |
| 5,571,170 A | 11/1996 | Palmaz et al. |
| 5,571,173 A | 11/1996 | Parodi |
| 5,571,174 A | 11/1996 | Love et al. |
| 5,578,071 A | 11/1996 | Parodi |
| 5,578,072 A | 11/1996 | Barone et al. |
| 5,582,168 A | 12/1996 | Samuels et al. |
| 5,591,229 A | 1/1997 | Parodi |
| 5,634,928 A | 6/1997 | Fischell et al. |
| 5,645,559 A | 7/1997 | Hachtman et al. |
| 5,653,749 A | 8/1997 | Love et al. |
| 5,683,451 A | 11/1997 | Lenker et al. |
| 5,713,953 A | 2/1998 | Vallana et al. |
| 5,728,152 A | 3/1998 | Mirsch, II et al. |
| 5,733,299 A | 3/1998 | Sheiban et al. |
| 5,741,333 A | 4/1998 | Frid |
| 5,746,775 A | 5/1998 | Levy et al. |
| 5,769,780 A | 6/1998 | Hata et al. |
| 5,782,914 A | 7/1998 | Schankereli |
| 5,787,887 A | 8/1998 | Klingenbeck-Regn |
| 5,840,081 A | 11/1998 | Andersen et al. |
| 5,855,601 A | 1/1999 | Bessler et al. |
| 5,861,028 A | 1/1999 | Angell |
| 5,862,806 A | 1/1999 | Cheung |
| 5,876,448 A | 3/1999 | Thompson et al. |
| 5,895,420 A | 4/1999 | Mirsch, II et al. |
| 5,931,969 A | 8/1999 | Carpentier et al. |
| 5,957,949 A | 9/1999 | Leonhardt et al. |
| 5,961,539 A | 10/1999 | Northrup, III et al. |
| 5,961,549 A | 10/1999 | Nguyen et al. |
| 5,972,030 A | 10/1999 | Garrison et al. |
| 5,976,179 A | 11/1999 | Inoue |
| 6,004,328 A | 12/1999 | Solar |
| 6,004,330 A | 12/1999 | Middleman et al. |
| 6,010,531 A | 1/2000 | Donlon et al. |
| 6,029,671 A | 2/2000 | Stevens et al. |
| 6,045,576 A | 4/2000 | Starr et al. |
| 6,053,938 A | 4/2000 | Goldmann et al. |
| 6,091,984 A | 7/2000 | Perelman et al. |
| 6,102,944 A | 8/2000 | Huynh et al. |
| 6,117,169 A | 9/2000 | Moe |
| 6,124,523 A | 9/2000 | Banas et al. |
| 6,125,852 A | 10/2000 | Stevens et al. |
| 6,126,686 A | 10/2000 | Badylak et al. |
| 6,129,756 A | 10/2000 | Kugler et al. |
| 6,162,245 A | 12/2000 | Jayaraman |
| 6,168,614 B1 | 1/2001 | Andersen et al. |
| 6,168,619 B1 | 1/2001 | Dinh et al. |
| 6,171,335 B1 | 1/2001 | Wheatley et al. |
| 6,174,327 B1 | 1/2001 | Mertens et al. |
| 6,186,999 B1 | 2/2001 | Chen |
| 6,197,143 B1 | 3/2001 | Bodnar |
| 6,214,055 B1 | 4/2001 | Simionescu et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,254,629 B1 | 7/2001 | Inoue |
| 6,254,630 B1 | 7/2001 | Inoue |
| 6,254,636 B1 | 7/2001 | Peredo |
| 6,264,691 B1 | 7/2001 | Gabbay |
| 6,269,819 B1 | 8/2001 | Oz et al. |
| 6,270,526 B1 | 8/2001 | Cox |
| 6,277,397 B1 | 8/2001 | Shimizu |

(56) References Cited

U.S. PATENT DOCUMENTS

| | | |
|---|---|---|
| 6,277,555 B1 | 8/2001 | Duran et al. |
| 6,287,335 B1 | 9/2001 | Drasler et al. |
| 6,293,970 B1 | 9/2001 | Wolfinbarger, Jr. et al. |
| 6,312,462 B1 | 11/2001 | McDermott et al. |
| 6,312,474 B1 | 11/2001 | Francis et al. |
| 6,334,873 B1 | 1/2002 | Lane et al. |
| 6,342,069 B1 | 1/2002 | Deac et al. |
| 6,350,278 B1 | 2/2002 | Lenker et al. |
| 6,350,282 B1 | 2/2002 | Eberhardt |
| 6,352,554 B2 | 3/2002 | De Paulis |
| 6,352,708 B1 | 3/2002 | Duran et al. |
| 6,358,275 B1 | 3/2002 | McIlroy et al. |
| 6,358,284 B1 | 3/2002 | Fearnot et al. |
| 6,371,980 B1 | 4/2002 | Rudakov et al. |
| 6,376,244 B1 | 4/2002 | Atala |
| 6,378,221 B1 | 4/2002 | Ekholm, Jr. et al. |
| 6,383,171 B1 | 5/2002 | Gifford et al. |
| 6,391,333 B1 | 5/2002 | Li et al. |
| 6,409,755 B1 | 6/2002 | Vrba |
| 6,418,339 B1 | 7/2002 | Essenpreis et al. |
| 6,425,916 B1 | 7/2002 | Garrison et al. |
| 6,432,712 B1 | 8/2002 | Wolfinbarger, Jr. |
| 6,440,167 B2 | 8/2002 | Shimizu |
| 6,458,153 B1 | 10/2002 | Bailey et al. |
| 6,461,382 B1 | 10/2002 | Cao |
| 6,468,313 B1 | 10/2002 | Claeson et al. |
| 6,471,723 B1 | 10/2002 | Ashworth et al. |
| 6,482,227 B1 | 11/2002 | Solovay |
| 6,482,228 B1 | 11/2002 | Norred |
| 6,482,240 B1 | 11/2002 | Eckmayer et al. |
| 6,491,719 B1 | 12/2002 | Fogarty et al. |
| 6,494,909 B2 | 12/2002 | Greenhalgh |
| 6,503,272 B2 | 1/2003 | Duerig et al. |
| 6,534,004 B2 | 3/2003 | Chen et al. |
| 6,540,782 B1 | 4/2003 | Snyders |
| 6,553,681 B2 | 4/2003 | Ekholm, Jr. et al. |
| 6,558,418 B2 | 5/2003 | Carpentier et al. |
| 6,565,960 B2 | 5/2003 | Koob et al. |
| 6,569,200 B2 | 5/2003 | Wolfinbarger, Jr. et al. |
| 6,582,458 B1 | 6/2003 | White et al. |
| 6,582,462 B1 | 6/2003 | Andersen et al. |
| 6,582,464 B2 | 6/2003 | Gabbay |
| 6,599,524 B2 | 7/2003 | Li et al. |
| 6,610,088 B1 | 8/2003 | Gabbay |
| 6,624,890 B2 | 9/2003 | Backman et al. |
| 6,626,938 B1 | 9/2003 | Butaric et al. |
| 6,652,577 B2 | 11/2003 | Gianotti |
| 6,652,578 B2 | 11/2003 | Bailey et al. |
| 6,666,886 B1 | 12/2003 | Tranquillo et al. |
| 6,676,698 B2 | 1/2004 | McGuckin, Jr. et al. |
| 6,682,537 B2 | 1/2004 | Ouriel et al. |
| 6,682,559 B2 | 1/2004 | Myers et al. |
| 6,685,739 B2 | 2/2004 | DiMatteo et al. |
| 6,696,074 B2 | 2/2004 | Dai et al. |
| 6,702,826 B2 | 3/2004 | Liddicoat et al. |
| 6,719,788 B2 | 4/2004 | Cox |
| 6,719,789 B2 | 4/2004 | Cox |
| 6,733,525 B2 | 5/2004 | Yang et al. |
| 6,736,823 B2 | 5/2004 | Darois et al. |
| 6,764,510 B2 | 7/2004 | Vidlund et al. |
| 6,773,456 B1 | 8/2004 | Gordon et al. |
| 6,773,457 B2 | 8/2004 | Ivancev et al. |
| 6,790,229 B1 | 9/2004 | Berreklouw |
| 6,792,979 B2 | 9/2004 | Konya et al. |
| 6,802,319 B2 | 10/2004 | Stevens et al. |
| 6,802,806 B2 | 10/2004 | McCarthy et al. |
| 6,821,297 B2 | 11/2004 | Snyders |
| 6,821,530 B2 | 11/2004 | Koob et al. |
| 6,830,584 B1 | 12/2004 | Seguin |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,608 B2 | 7/2005 | Liddicoat et al. |
| 6,916,338 B2 | 7/2005 | Speziali |
| 6,942,694 B2 | 9/2005 | Liddicoat et al. |
| 6,951,571 B1 | 10/2005 | Srivastava |
| 6,961,123 B1 | 11/2005 | Wang et al. |
| 6,977,231 B1 | 12/2005 | Matsuda |
| 6,986,735 B2 | 1/2006 | Abraham et al. |
| 7,004,925 B2 | 2/2006 | Navia et al. |
| 7,008,763 B2 | 3/2006 | Cheung |
| 7,011,688 B2 | 3/2006 | Gryska et al. |
| 7,018,404 B2 | 3/2006 | Holmberg et al. |
| 7,018,406 B2 | 3/2006 | Seguin et al. |
| 7,022,348 B2 | 4/2006 | Ketharanathan |
| 7,025,780 B2 | 4/2006 | Gabbay |
| 7,037,333 B2 | 5/2006 | Myers et al. |
| 7,039,446 B2 | 5/2006 | Ruchti et al. |
| 7,041,132 B2 | 5/2006 | Quijano et al. |
| 7,053,051 B2 | 5/2006 | Hendriks et al. |
| 7,060,092 B2 | 6/2006 | Kuribayashi et al. |
| 7,070,616 B2 | 7/2006 | Majercak et al. |
| 7,077,862 B2 | 7/2006 | Vidlund et al. |
| 7,084,082 B1 | 8/2006 | Shimizu |
| 7,138,226 B2 | 11/2006 | Vincek et al. |
| 7,153,324 B2 | 12/2006 | Case et al. |
| 7,160,322 B2 | 1/2007 | Gabbay |
| 7,164,145 B2 | 1/2007 | Shakespeare |
| 7,166,570 B2 | 1/2007 | Hunter et al. |
| 7,189,259 B2 | 3/2007 | Simionescu et al. |
| 7,213,601 B2 | 5/2007 | Stevens et al. |
| 7,214,242 B2 | 5/2007 | Abraham et al. |
| 7,232,461 B2 | 6/2007 | Ramer |
| 7,261,732 B2 | 8/2007 | Justino |
| 7,289,211 B1 | 10/2007 | Walsh, Jr. et al. |
| 7,309,461 B2 | 12/2007 | Kujawski et al. |
| 7,311,730 B2 | 12/2007 | Gabbay |
| 7,318,998 B2 | 1/2008 | Goldstein et al. |
| 7,329,279 B2 | 2/2008 | Haug et al. |
| 7,331,993 B2 | 2/2008 | White |
| 7,354,702 B2 | 4/2008 | Dai et al. |
| RE40,404 E | 6/2008 | Schmitt et al. |
| 7,381,218 B2 | 6/2008 | Schreck |
| 7,381,219 B2 | 6/2008 | Salahieh et al. |
| 7,399,315 B2 | 7/2008 | Iobbi |
| 7,427,291 B2 | 9/2008 | Liddicoat et al. |
| 7,431,725 B2 | 10/2008 | Stack et al. |
| 7,468,073 B2 | 12/2008 | Johnson et al. |
| 7,473,237 B2 | 1/2009 | Navia et al. |
| 7,481,838 B2 | 1/2009 | Carpentier et al. |
| 7,503,929 B2 | 3/2009 | Johnson et al. |
| 7,510,571 B2 | 3/2009 | Spiridigliozzi et al. |
| 7,510,575 B2 | 3/2009 | Spenser et al. |
| 7,524,330 B2 | 4/2009 | Berreklouw |
| 7,556,646 B2 | 7/2009 | Yang et al. |
| 7,566,343 B2 | 7/2009 | Jenson et al. |
| 7,585,321 B2 | 9/2009 | Cribier |
| 7,604,661 B2 | 10/2009 | Pavcnik et al. |
| 7,618,446 B2 | 11/2009 | Andersen et al. |
| 7,622,276 B2 | 11/2009 | Cunanan et al. |
| 7,628,805 B2 | 12/2009 | Spenser et al. |
| 7,648,676 B2 | 1/2010 | Mills et al. |
| 7,670,368 B2 | 3/2010 | Hill et al. |
| 7,704,277 B2 | 4/2010 | Zakay et al. |
| 7,708,775 B2 | 5/2010 | Rowe et al. |
| 7,758,632 B2 | 7/2010 | Hojeibane et al. |
| 7,780,722 B2 | 8/2010 | Thielen et al. |
| 7,789,909 B2 | 9/2010 | Andersen et al. |
| 7,846,203 B2 | 12/2010 | Cribier |
| 7,846,204 B2 | 12/2010 | Letac et al. |
| 7,871,431 B2 | 1/2011 | Gurm et al. |
| 7,892,281 B2 | 2/2011 | Seguin et al. |
| 7,914,569 B2 | 3/2011 | Nguyen et al. |
| 7,914,576 B2 | 3/2011 | Navia et al. |
| RE42,395 E | 5/2011 | Wright et al. |
| 7,967,833 B2 | 6/2011 | Sterman et al. |
| 7,981,151 B2 | 7/2011 | Rowe |
| 7,993,394 B2 | 8/2011 | Hariton et al. |
| 8,002,825 B2 | 8/2011 | Letac et al. |
| 8,007,992 B2 | 8/2011 | Tian et al. |
| 8,052,750 B2 | 11/2011 | Tuval et al. |
| 8,057,540 B2 | 11/2011 | Letac et al. |
| 8,080,054 B2 | 12/2011 | Rowe |
| 8,105,375 B2 | 1/2012 | Navia et al. |

(56) References Cited

U.S. PATENT DOCUMENTS

| | | |
|---|---|---|
| 8,313,525 B2 | 11/2012 | Tuval et al. |
| 8,348,995 B2 | 1/2013 | Tuval et al. |
| 8,348,996 B2 | 1/2013 | Tuval et al. |
| 8,414,643 B2 | 4/2013 | Tuval et al. |
| 8,512,401 B2 | 8/2013 | Murray, III et al. |
| 8,512,403 B2 | 8/2013 | Navia et al. |
| 8,568,475 B2 | 10/2013 | Nguyen et al. |
| 8,579,964 B2 | 11/2013 | Lane et al. |
| 8,628,566 B2 | 1/2014 | Eberhardt et al. |
| 8,758,432 B2 | 6/2014 | Solem |
| 8,834,563 B2 | 9/2014 | Righini |
| 8,834,564 B2 | 9/2014 | Tuval et al. |
| 8,876,894 B2 | 11/2014 | Tuval et al. |
| 8,876,895 B2 | 11/2014 | Tuval et al. |
| 8,992,608 B2 | 3/2015 | Haug et al. |
| 9,119,716 B2 | 9/2015 | Lee et al. |
| 9,119,738 B2 | 9/2015 | Fish |
| 9,186,248 B2 | 11/2015 | Paniagua et al. |
| 9,393,110 B2 | 7/2016 | Levi et al. |
| 9,504,564 B2 | 11/2016 | Nguyen et al. |
| 9,737,400 B2 | 8/2017 | Fish et al. |
| 9,848,981 B2 | 12/2017 | Suri et al. |
| 2001/0010017 A1 | 7/2001 | Letac et al. |
| 2001/0023372 A1 | 9/2001 | Chen et al. |
| 2001/0049558 A1 | 12/2001 | Liddicoat et al. |
| 2002/0005073 A1 | 1/2002 | Tompkins et al. |
| 2002/0028243 A1 | 3/2002 | Masters |
| 2002/0029783 A1 | 3/2002 | Stevens et al. |
| 2002/0032481 A1 | 3/2002 | Gabbay |
| 2002/0037940 A1 | 3/2002 | Koob et al. |
| 2002/0042621 A1 | 4/2002 | Liddicoat et al. |
| 2002/0091441 A1 | 7/2002 | Guzik |
| 2002/0095167 A1 | 7/2002 | Liddicoat et al. |
| 2002/0095994 A1 | 7/2002 | Vesely et al. |
| 2002/0123789 A1 | 9/2002 | Francis et al. |
| 2002/0128708 A1 | 9/2002 | Northrup et al. |
| 2002/0151970 A1 | 10/2002 | Garrison et al. |
| 2003/0027332 A1 | 2/2003 | Lafrance et al. |
| 2003/0078659 A1 | 4/2003 | Yang |
| 2003/0102000 A1 | 6/2003 | Stevens et al. |
| 2003/0130727 A1 | 7/2003 | Drasler et al. |
| 2003/0130729 A1 | 7/2003 | Paniagua et al. |
| 2003/0130731 A1 | 7/2003 | Vidlund et al. |
| 2003/0149477 A1 | 8/2003 | Gabbay |
| 2003/0153974 A1 | 8/2003 | Spenser et al. |
| 2003/0187362 A1 | 10/2003 | Murphy et al. |
| 2003/0195620 A1 | 10/2003 | Huynh et al. |
| 2003/0204023 A1 | 10/2003 | Koob et al. |
| 2003/0209835 A1 | 11/2003 | Chun et al. |
| 2003/0212460 A1 | 11/2003 | Darois et al. |
| 2003/0212462 A1 | 11/2003 | Gryska et al. |
| 2003/0217415 A1 | 11/2003 | Crouch et al. |
| 2004/0024452 A1 | 2/2004 | Kruse et al. |
| 2004/0039442 A1 | 2/2004 | St. Goar et al. |
| 2004/0055608 A1 | 3/2004 | Stevens et al. |
| 2004/0059418 A1 | 3/2004 | McKay et al. |
| 2004/0098092 A1 | 5/2004 | Butaric et al. |
| 2004/0158321 A1 | 8/2004 | Reuter et al. |
| 2004/0193261 A1 | 9/2004 | Berreklouw |
| 2004/0230285 A1 | 11/2004 | Gifford et al. |
| 2004/0243153 A1 | 12/2004 | Liddicoat et al. |
| 2004/0243229 A1 | 12/2004 | Vidlund et al. |
| 2005/0004668 A1 | 1/2005 | Aklog et al. |
| 2005/0027369 A1 | 2/2005 | Eldridge et al. |
| 2005/0043819 A1 | 2/2005 | Schmidt et al. |
| 2005/0096673 A1 | 5/2005 | Stack et al. |
| 2005/0113910 A1 | 5/2005 | Paniagua et al. |
| 2005/0137681 A1 | 6/2005 | Shoemaker et al. |
| 2005/0137682 A1 | 6/2005 | Justino |
| 2005/0142163 A1 | 6/2005 | Hunter et al. |
| 2005/0147562 A1 | 7/2005 | Hunter et al. |
| 2005/0147599 A1 | 7/2005 | Hunter et al. |
| 2005/0147643 A1 | 7/2005 | Hunter et al. |
| 2005/0148512 A1 | 7/2005 | Hunter et al. |
| 2005/0158274 A1 | 7/2005 | Hunter et al. |
| 2005/0159811 A1 | 7/2005 | Lane |
| 2005/0169958 A1 | 8/2005 | Hunter et al. |
| 2005/0169959 A1 | 8/2005 | Hunter et al. |
| 2005/0175657 A1 | 8/2005 | Hunter et al. |
| 2005/0187618 A1 | 8/2005 | Gabbay |
| 2005/0191248 A1 | 9/2005 | Hunter et al. |
| 2005/0228494 A1 | 10/2005 | Marquez |
| 2005/0241981 A1 | 11/2005 | Gupta et al. |
| 2005/0246035 A1 | 11/2005 | Wolfinbarger et al. |
| 2005/0247320 A1 | 11/2005 | Stack et al. |
| 2005/0267529 A1 | 12/2005 | Crockett et al. |
| 2006/0004439 A1 | 1/2006 | Spenser et al. |
| 2006/0004443 A1 | 1/2006 | Liddicoat et al. |
| 2006/0020336 A1 | 1/2006 | Liddicoat |
| 2006/0025800 A1 | 2/2006 | Suresh |
| 2006/0041306 A1 | 2/2006 | Vidlund et al. |
| 2006/0074486 A1 | 4/2006 | Liddicoat et al. |
| 2006/0089708 A1 | 4/2006 | Osse et al. |
| 2006/0111733 A1 | 5/2006 | Shriver |
| 2006/0129225 A1 | 6/2006 | Kopia et al. |
| 2006/0134079 A1 | 6/2006 | Sih et al. |
| 2006/0140916 A1 | 6/2006 | Siani-Rose et al. |
| 2006/0173475 A1 | 8/2006 | Lafontaine et al. |
| 2006/0178740 A1 | 8/2006 | Stacchino et al. |
| 2006/0190074 A1 | 8/2006 | Hill et al. |
| 2006/0193885 A1 | 8/2006 | Leonard Neethling et al. |
| 2006/0195010 A1 | 8/2006 | Amal et al. |
| 2006/0195183 A1 | 8/2006 | Navia et al. |
| 2006/0206203 A1 | 9/2006 | Yang et al. |
| 2006/0229701 A1 | 10/2006 | Gurm et al. |
| 2006/0240063 A9 | 10/2006 | Hunter et al. |
| 2006/0240064 A9 | 10/2006 | Hunter et al. |
| 2006/0259134 A1 | 11/2006 | Schwammenthal et al. |
| 2006/0259135 A1 | 11/2006 | Navia et al. |
| 2006/0259137 A1 | 11/2006 | Artof et al. |
| 2006/0265056 A1 | 11/2006 | Nguyen et al. |
| 2006/0287571 A1 | 12/2006 | Gozzi et al. |
| 2006/0292125 A1 | 12/2006 | Kellar et al. |
| 2007/0010857 A1 | 1/2007 | Sugimoto et al. |
| 2007/0043431 A1 | 2/2007 | Melsheimer |
| 2007/0050014 A1 | 3/2007 | Johnson |
| 2007/0050022 A1 | 3/2007 | Vidlund et al. |
| 2007/0056346 A1 | 3/2007 | Spenser et al. |
| 2007/0060932 A1 | 3/2007 | Stack et al. |
| 2007/0061008 A1 | 3/2007 | Salahieh et al. |
| 2007/0100426 A1 | 5/2007 | Rudakov et al. |
| 2007/0104395 A1 | 5/2007 | Kinigakis et al. |
| 2007/0128174 A1 | 6/2007 | Kleinsek et al. |
| 2007/0173861 A1 | 7/2007 | Strommer et al. |
| 2007/0203575 A1 | 8/2007 | Forster et al. |
| 2007/0213813 A1 | 9/2007 | Von Segesser et al. |
| 2007/0233228 A1 | 10/2007 | Eberhardt et al. |
| 2007/0250154 A1 | 10/2007 | Greenberg et al. |
| 2007/0263226 A1 | 11/2007 | Kurtz et al. |
| 2007/0276432 A1 | 11/2007 | Stack et al. |
| 2007/0276461 A1 | 11/2007 | Andreas et al. |
| 2008/0004686 A1 | 1/2008 | Hunt et al. |
| 2008/0009667 A1 | 1/2008 | Longhini et al. |
| 2008/0009940 A1 | 1/2008 | Cribier |
| 2008/0029105 A1 | 2/2008 | Stevens et al. |
| 2008/0039871 A1 | 2/2008 | Wallace et al. |
| 2008/0039926 A1 | 2/2008 | Majercak et al. |
| 2008/0058798 A1 | 3/2008 | Wallace et al. |
| 2008/0082113 A1 | 4/2008 | Bishop et al. |
| 2008/0102439 A1 | 5/2008 | Tian et al. |
| 2008/0133004 A1 | 6/2008 | White |
| 2008/0147182 A1 | 6/2008 | Righini et al. |
| 2008/0154356 A1 | 6/2008 | Obermiller et al. |
| 2008/0177381 A1 | 7/2008 | Navia et al. |
| 2008/0183280 A1 | 7/2008 | Agnew et al. |
| 2008/0183283 A1 | 7/2008 | Downing |
| 2008/0190989 A1 | 8/2008 | Crews et al. |
| 2008/0195200 A1 | 8/2008 | Vidlund et al. |
| 2008/0199843 A1 | 8/2008 | Haverich et al. |
| 2008/0200977 A1 | 8/2008 | Paul et al. |
| 2009/0005857 A1 | 1/2009 | Ischinger |
| 2009/0030511 A1 | 1/2009 | Paniagua et al. |
| 2009/0043383 A1 | 2/2009 | McGregor et al. |
| 2009/0054969 A1 | 2/2009 | Salahieh et al. |

(56) References Cited

U.S. PATENT DOCUMENTS

| | | |
|---|---|---|
| 2009/0062907 A1 | 3/2009 | Quijano et al. |
| 2009/0112309 A1 | 4/2009 | Jaramillo et al. |
| 2009/0132032 A9 | 5/2009 | Cribier |
| 2009/0157175 A1 | 6/2009 | Benichou |
| 2009/0164005 A1 | 6/2009 | Dove et al. |
| 2009/0187241 A1 | 7/2009 | Melsheimer |
| 2009/0248149 A1 | 10/2009 | Gabbay |
| 2009/0254175 A1 | 10/2009 | Quijano et al. |
| 2009/0281609 A1 | 11/2009 | Benichou et al. |
| 2010/0030259 A1 | 2/2010 | Pavcnik et al. |
| 2010/0036479 A1 | 2/2010 | Hill et al. |
| 2010/0036484 A1 | 2/2010 | Hariton et al. |
| 2010/0043197 A1 | 2/2010 | Abbate et al. |
| 2010/0048987 A1 | 2/2010 | Khairkhahan |
| 2010/0049312 A1 | 2/2010 | Edoga et al. |
| 2010/0131054 A1 | 5/2010 | Tuval et al. |
| 2010/0161036 A1 | 6/2010 | Pintor et al. |
| 2010/0185277 A1 | 7/2010 | Braido et al. |
| 2010/0217382 A1 | 8/2010 | Chau et al. |
| 2010/0234878 A1 | 9/2010 | Hruska et al. |
| 2010/0241069 A1 | 9/2010 | Hatten |
| 2010/0249918 A1 | 9/2010 | Zhang |
| 2010/0256749 A1 | 10/2010 | Tran et al. |
| 2010/0256751 A1 | 10/2010 | Rowe et al. |
| 2010/0312333 A1 | 12/2010 | Navia et al. |
| 2011/0004299 A1 | 1/2011 | Navia et al. |
| 2011/0015728 A1 | 1/2011 | Jimenez et al. |
| 2011/0040375 A1 | 2/2011 | Letac et al. |
| 2011/0087322 A1 | 4/2011 | Letac et al. |
| 2011/0137409 A1 | 6/2011 | Yang et al. |
| 2011/0146361 A1 | 6/2011 | Davidson et al. |
| 2011/0153009 A1 | 6/2011 | Navia et al. |
| 2011/0166636 A1 | 7/2011 | Rowe |
| 2011/0178597 A9 | 7/2011 | Navia et al. |
| 2011/0218619 A1 | 9/2011 | Benichou et al. |
| 2011/0224607 A1 | 9/2011 | Vogelbaum et al. |
| 2011/0240511 A1 | 10/2011 | Bolton et al. |
| 2011/0300625 A1 | 12/2011 | Paniagua et al. |
| 2011/0301700 A1 | 12/2011 | Fish et al. |
| 2012/0078343 A1 | 3/2012 | Fish |
| 2012/0078356 A1 | 3/2012 | Fish et al. |
| 2012/0095551 A1 | 4/2012 | Navia et al. |
| 2012/0158128 A1 | 6/2012 | Gautam et al. |
| 2012/0185038 A1 | 7/2012 | Fish et al. |
| 2012/0310041 A1 | 12/2012 | Paniagua et al. |
| 2013/0018458 A1 | 1/2013 | Yohanan et al. |
| 2013/0204347 A1 | 8/2013 | Armstrong et al. |
| 2013/0304201 A1 | 11/2013 | Navia et al. |
| 2014/0039613 A1 | 2/2014 | Navia et al. |
| 2014/0324154 A1* | 10/2014 | Shalev ............... A61F 2/82 623/1.13 |
| 2017/0014229 A1 | 1/2017 | Nguyen-Thien-Nhon et al. |
| 2017/0049566 A1 | 2/2017 | Zeng et al. |
| 2019/0076245 A1 | 3/2019 | Arcaro et al. |

FOREIGN PATENT DOCUMENTS

| | | |
|---|---|---|
| EP | 1441672 | 9/2011 |
| EP | 2055266 | 2/2012 |
| EP | 1621162 | 5/2012 |
| EP | 2260796 | 2/2013 |
| EP | 2219558 B1 | 8/2015 |
| RU | 2355361 C | 5/2009 |
| WO | 1991/017720 | 11/1991 |
| WO | 1992/017118 | 10/1992 |
| WO | 1998/029057 | 7/1998 |
| WO | 1999/030646 | 6/1999 |
| WO | 2000/012164 | 3/2000 |
| WO | 2001/002031 | 1/2001 |
| WO | 2003/047468 | 6/2003 |
| WO | 2003/092554 | 11/2003 |
| WO | 2004/026124 | 4/2004 |
| WO | 2004/082527 | 9/2004 |
| WO | 2006/095342 | 9/2006 |
| WO | 2007/138572 | 12/2007 |
| WO | 2008/082527 | 7/2008 |
| WO | 2008/063537 | 8/2008 |
| WO | 2008/106531 | 9/2008 |
| WO | 2009/052188 | 4/2009 |
| WO | 2009/156471 | 12/2009 |
| WO | 2010/024801 | 3/2010 |
| WO | 2010/027363 | 3/2010 |
| WO | 2010/080594 | 7/2010 |
| WO | 2010/117541 | 10/2010 |
| WO | 2011/109433 | 3/2011 |
| WO | 2011/109450 | 9/2011 |
| WO | 2012/006124 | 1/2012 |
| WO | 2012/040643 | 3/2012 |
| WO | 2012/082952 | 6/2012 |

OTHER PUBLICATIONS

Andersen, H.R. et al., "Transluminal implantation of artificial heart valve" European Heart Journal, 1992, 13, pp. 704-708.

"Artificial heart valve" http://en.wikipedia.org/Artificial_heart_valve, printed May 13, 2009.

Bech-Hanssen, Odd, M.D. et al., "Aortic Prosthetic Valve Desing and Size: Relation to Doppler Echocardiographic Finding and Pressure Recovery—An In Vitro Study" J. Am Soc Echocardiography 2000; vol. 13, pp. 39-50.

Bonhoeffer, Philipp M.D. et al., "Percutaneous Insertion of the Pulmonary Valve" J of the Amer College of Cardiology, vol. 39, No. 10, Elsevier Science, Inc. 2002, pp. 1664-1669, London, UK, and Paris, FR.

Bonhoeffer, Philipp et al., "Percutaeous replacement of pulmonary valve in a right-centricle to pulmonary-artery prosthetic conduit with valve dysfunction" Early Report, The Lacet, vol. 356, Oct. 21, 2000, p. 1403-1405.

Bonhoeffer, Philipp et al., "Transcatherter Implantation of a Bovine Valve in Pulmonary Position: A Lamb Study" Circulation J. of the Amer Heart Assoc, 2000; 102; pp. 813-816.

Boudjemline, Younes et al., "Percutaneous pulmonary valve replacement in a large right ventricular outflow tract: An experimental study" J. Am. Coll. Cardiol. 2004; 43; pp. 1082-1087.

Braga-Vilela, A. et al., "Extracellular Matrix of Porcine Pericardium; Biochemistry and Collagen Architecture" J. Membr Biol., 2008.

Breuer, Christopher K. M.D. et al., "Application of Tissue-Engineering Principles toward the Development of a Semilunar Heart Valve Substitute" Tissue Engineering, vol. 10, No. 11/12, 2004, pp. 1725-1736.

Cale, A.R. et al., "Revisited: a descending thoracic aortic valve to treat prosthetic valve insufficiency" Ann Thorac Surg, May 1993, 55(5), pp. 1218-2.

Cerrolaza, M et al., "A comparison of the hydrodynamical behaviour of three heart aortic prostheses by numerical methods" Journal of Medical Engineering & Technology, vol. 20, No. 6, Nov./Dec. 1996, pp. 219-228.

Chew, G.G. et al., Abstract for "Simulation of Damage in a Porcine Prosthetic Heart Valve" J. Med. Eng. Technol., Sep.-Oct. 1999; 23(5): 178-89 (Abstract only).

Christie G.W. et al., Abstract for "On Stress Reduction in Bioprosthetic Heart Valve Leaflets by the Use of a Flexible Stent" J. Card Surg, Dec. 1991; 6(4) pp. 476-481 (Abstract only).

"Collagen" http://en.wikipedia.org/wiki/Collagen, printed May 13, 2009.

Collins, J. J., Jr, "The Evolution of artificial heart valve" N. Engl J Med, Feb. 28, 1991; vol. 324(9), pp. 624-626.

Corden, J. et al., "The influence of open leaflet geometry on the haemodynamic flow characteristics of polyrethane trileaflet artificial heart valve" Journal of Engineering in Medicine, 1996., vol. 210, pp. 273-287.

Cribier, Alain et al., "Percutaneious Transcatheter Implantation of an Aoritc Valve Prosthesis for Calcific Aortic Stenosis: First Human Case Description" Circulation J of the Amer Heart Assoc, originally published online Nov. 25, 2002.

(56) References Cited

OTHER PUBLICATIONS

Edwards Lifesciences Receives FDA Approval for New Heart Valve, http:www.medicalnewstoday.com/articles/149588.php, May 11, 2009.
Fish, R. David, "Percutaneous Heart Valve Replacement: Enthusiasm Tempered" Circulation J of the Amer Heart Assoc, 2004; vol. 110; pp. 1876-1878.
Fishbein, M.C. et al., "Cardiac pathology after aortic valve replacement using Hufnagel trileaflet prostheses: study of 20 necropsy patients" Ann Heart J., Apr. 1975, 89(4), pp. 443-448.
Gloeckner, D. Claire et al., "Mechanical Evaluation and Design of a Multilayered Collagenous Repair Biomaterial" J. of Biomedical Materials Research Part A, vol. 52 Iss 2, pp. 365-373, Published online Aug. 15, 2000, Wiley Periodicals, Inc.
Grube, et al., "Progress and Current Status of Percutaneous Aortic Valve Replacement: Results of Three Device Generations of the CoreValve Revalving System", Circ. Cardiovasc Intervent 2008;1:167-175 (Abstract only).
Hanlon, JG et al., "Pre-use intraoperative testing of autologous tissue for valvular surgery: a proof of concept study" J. Heart Valve Dis, Nov. 1999; 8(6); pp. 614-623.
Hasenkam, J.M. et al., "A model for acute haemodynamic studies in the ascending aorta in pigs" Cardiovasc Res, Jul. 1988, 22(7), pp. 464-471.
Hiester,E.D. et al., "Optimal bovine pericardial tissue selection sites. I. Fiber architecture and tissue thickness measurements." J. Biomed Mater Res, Feb. 1, 1998; 39(2), pp. 207-214.
Hilbert et al., "Biometrics: Allograft Heart Valves," Cardiac Reconstructions with Allograft Tissues, Springer, New York (2005), pp. 210-212.
Hufnagel, Charles A., M.D., "Basic Concepts in the Development of Cardiovascular Prosthes" The American Journal of Surgery, vol. 137, Mar. 1979.
Hufnagel, Charles.A., MD et al., "In the beginning. Surgical Correction of Aortic Insufficiency" 1954; Ann Thorac Surg May 1989; 47(3), pp. 475-476.
Hufnagel, Charles.A., MD et al., "Late follow-up of ball-valve prostheses in the descending thoracic aortia", J. Throrac Cardiovasc Surg, Dec. 1976, 72(6), pp. 900-909.
Hufnagel, Charles.A., MD et al., "Surgical Correction of Aortic Insufficiency" Surgery vol. 35, May 1954 No. 5.
Hufnagel, Charles A., "Vessels and Valves", Sec. 1: Development of Cardiac Surgery, 2nd ed., 1975, Chap 7, pp. 43-55.
Introduction to Stereomicroscopy, http://www.microscopyu.com/articles/stereomicroscopy/stereointro.html, Copyright 2000-2012, printed on Mar. 15, 2012.
IOPATCH(R) Tutoplast(R) Processed Pericardium Directions for Use; http://www.iopinc.com/surgeons_and_medical_professionals/iopatch/directions.asp, printed on Jun. 2, 2009.
Knudsen, LL et al., "Catheter-implanted prosthetic heart valves. Transluminal catheter implantation of a new expandable artificial heart valve in the descending thoracic aorta in isolated vessels and closed chest pigs" Int J. Artif Organs, May 1993, 16(5); pp. 253-262.
Lax, Jorge A., M.D., et al. "Estimation of the Ejection Fraction in Patients with Myocardial Infarction Obtained from the Combined Index of Systolic and Diastolic Left Ventricular Function: A New Method" J of the American Soc of Echocardiography, Feb. 2000, vol. 13, No. 2, pp. 116-123.
Liao, K X et al., "Two-dimensional mechanical and ultrastructural correlates of bovine pericardium for prosthetic valves" ASAIO Trans, Jun. 1, 1991, 37(3); M341-51.
Liao, Jun et al., "Molecular orientation of collagen in intact planar connective tissues under biaxial stretch" Acta Biomateriala, vol. 1, Iss. 1, Jan. 2005, pp. 45-54.
Mendelson, Karen et al., "Heart Valve Tissue Engineering: Concepts, Approaches, Progress, and Challenges" Ann Biomed Eng, Dec. 2006; 34(12); pp. 1799-1819; published online Oct. 12, 2006 doi:10.1007/s/10439-006-9163-z.
Mirnajafi, A. et al. "The effects of collagen fiber orientation of the flexural properties of pericardial heterograft biomaterials" Biomaterials, Mar. 2005; 26(7): pp. 795-804.
Mirzaie, M. et al., "A new storage solution for porcine aortic valves" Ann Thorac Cardiovasc Surg. Apr. 2007;13(2), pp. 102-109.
Moazami, N. et al., "Transluminal aortic valve placement. A feasibility study with a newly designed collapsible aortic valve" ASAIO J, Sep.-Oct. 1996, 42(5):M 381-5.
Nienaber C., M.D. et al., "Nonsurgical Reconstruction of Thoracic Aortic Dissection By Stent-Graft Placement" N. Eng. J. Med, May 20, 1999, col. 340, No. 20.
Noorlander, Maril L. et al., "A Quantitative Method to Determine the Orientation of Collagen Fibers in the Dermis" The J. of Histochemistry & Cytochemistry, vol. 50(11): 2002, pp. 1469-1474.
Nunn, D.B., "Structural Failure of Dacron Arterial Grafts" Seminars in Vascular Surgery, col. 12, No. 1 (March), 1999, pp. 88-91.
Optical Microscope, Wikipedia, http://en.wikipedia.org/wiki/Stereomiscroscope, May 13, 2009.
Orthogonality, http://en.wikipedia.org/wiki/Orthogonal, May 13, 2009.
Paniagua, David et al.. Abstract 4622: "Percutaneous Implantation of a Low Profile, Dry Membrane, Heart Valve in an Integrated Delivery System in the Aortic and Pulmonary Positions: One-month Animal Results," Circulation, American Heart Association, Inc., 2009; vol. 120: pp. 982.
Paniagua, David, et al., Percutaneous Heart Valve in the Chronic In Vitro Testing Model, Circulation, 2002, pp. 51-52, vol. 106, American Heart Association, US.
Paniagua, David et al., First Human Case of Retrograde Transcatheter Implantation of an Aortic Valve Prosthesis, Texas Heart Institute Journal, 2005, pp. 91-96, vol. 32, US.
Pathak, CP et al., "Treatment of bioprosthetic heart valve tissue with long chain alcohol solution to lower calcification potential" J Biomed Mater Res A. Apr. 1, 2004;69(1), pp. 140-144.
Pavenik, Susan, M.D., PhD et al., "Development and Initial Experimental Evaluation of a Prosthetic Aortic Valve for Transcatherter Placement" Cardiovascular Radiology, Apr. 1992, pp. 151-154.
Pohl, M. et al., "In vitro testing of artificial heart valves; comparison between Newtonian and non-Newtonian fluids" Artif Argns, Jan. 1996; 20(1); pp. 37-46.
Pick, Adam, "True or False: An Edwards Lifesciences' Tissue Valve Replacement Requires 1,800 Hand-Sewn Stitches" http://heart-valve-surgery.com/heart-surgery-blog/2008/02/26. printed Aug. 13, 2010.
Purinya, B. et al., "Biomechanical and Structural Properties of the Explanted Bioprosthetic Valve Leaflets" J. of Biomechanis, vol. 27, Iss 1, Jan. 1994 pp. 1-11 Elsevier Science Ltd, 1993.
Sacks, M S et al., "Bioprosthetic heart valve heterograft biomaterials: structure, mechanical behavior and computational simulation" Expert Rev Med Devices, Nov. 2006; 3(6): pp. 817-834 (Abstract only).
Sacks, M S et al., "Collagen fiber architecture of bovine pericardium" ASAIO J, Jul. 1, 1994, 40(3), pp. 632-637.
Sacks, M S et al., "A small angle light scattering device for planar connective tissue miscrostructural analysis" Ann Biomed Eng, Jul. 1, 1997, 254(4), pp. 678-689.
Sacks, Michael S. et al., "Quantification of the fiber architecture and biaxial mechanical behavior of porcine intestinal submucosa" J of Biomedical Research, vol. 46, Iss 1, Jul. 1999, pp. 1-10.
Sacks, Michael S, "Incorporation of experimentally-derived fiber orientation into a structural constitutive model for planar collagenous tissues" J. Biomech Eng, Apr. 1, 2003, 125(2), pp. 280-287.
Samouillan, V. et al., "Comparison of chemical treatments on the chain dynamics and thermal stability of bovine pericardium collagen" J Biomed Mater Res A. Feb. 1, 2003 ;64(2), pp. 330-338.
Schmidt, Dorthe et al., "Tissue engineering of heart valves using decellularized xenogeneic of polymeric starter matrices" Philos Trans R Soc Lond B Bio Sci., Aug. 29, 2007, 362(1484); 1505-1512; published online Jun. 22, 2007, doi: 10.1098/rstb.2007.2131.
Schoen, Frederick J., "Tissue heart valves: Current challenges and future research perspectives" J of Biomedical Materials Research, vol. 47, Iss 4, Dec. 15, 1999, pp. 439-465.

(56) References Cited

OTHER PUBLICATIONS

Sellaro, Tiffany L., "Effects of Collagen Orientation on the Medium-Term Fatigue Response of Heart Valve Biomaterials" 2003, (published thesis) pp. 40-45.

Sellaro, Tiffany L. et al., "Effects of Collagen Fiber Orientation on the Response of Biologically Derived Soft Tissue Biomaterials to Cyclic Loading" J. Biomed Mater Res A Jan. 1, 2007; 80(1): 194-205); published online Oct. 13, 2006 by Wiley InterScience.

Shandas, Robin PhD et al., "A Method for Determining the Reference Effective Flow Areas for Mechanical Heart Valve Prostheses" Circulation Apr. 25, 2000.

Shen, Ming et al., "Effect of ethanol and ether in the prevention of calcification of bioprostheses" Ann Thorac Surg. May 2001;71(5 Suppl), pp. 413-416.

Shen, Ming et al., "Protein adsorption in glutaraldehyde-preserved bovine pericardium and porcine valve tissues" The Annals of Thoracic Surgery, 2001; 71, pp. 409.

Simionescu, D et al., "Mapping of glutaraldehyde-treated bovine pericardium and tissue selection for bioprosthetic heart valve" J. Biomed Mater Res, Jun. 1, 1993:27(6), pp. 697-704.

Sun, Wei et al., "Response of heterograft heart valve biomaterials to moderate cyclic loading" J Biomed Mater Res A, Jun. 2004, 69(4), pp. 658-669.

Topol, Eric J., "Textbook of Interventional Cardiology", 1990, Chs. 43-44, pp. 831-867.

Vyavahare, Narendra et al., "Mechanisms of bioprosthetic heart valve failure: Fatigue causes collagen denaturation and glycosaminoglysan loss" J of Biomedical Research, vol. 446, Iss 1, Jul. 1999, pp. 44-50.

Vyavahare, NR et al., "Prevention of Glutaraldehyde-Fixed Bioprosthetic Heart Valve Calcification by Alcohol Pretreatment: Further Mechanistic Studies" J Heart Valve Dis Jul. 2000;9(4), pp. 561-566.

Werner, S. et al., "Testing the Hydrodynamic properties of heart valve prostheses with a new test apparatus", Biomed Tech (Berl) Sep. 1994; 30(9); pp. 204-210 (Abstract only).

Wiegner, A W et al., "Mechanical and structural correlates of canine pericardium" Circ Res, Sep. 1,1981m 49(3), pp. 807-814.

Yasui, Takeshi et al., "Determination of collagen fiber orientation in human tissue by use of polarization measurement of molecular second-harmonic-generation light", Applied Optics, vol. 42, No. 14, May 10, 2004, pp. 2861-2867.

Yu, L.S. et al., "New Polyurethane valves in new soft artificial heart" ASAIO Trans Jul.-Sep. 1989; 35(3), pp. 301-304.

Zioupos, P. et al., "Anisotropic Elasticity and Strength of Glutaraldehyde Fixed Bovine Pericardium for Use in Pericardial Bioprosthetic Valves" J Biomed Mater Res., Jan. 1994, 28(1), pp. 49-57.

Zioupos, P. et al., "Mechanical and Optical anisotrophy of bovine pericardium" Med Biol Eng Comput, Jan. 1992; (1); pp. 76-82.

PCT Written Opinion, in Application PCT/US2011/026741, dated Nov. 28, 2011.

International Search Report and Written Opinion, in Application PCT/US2011/053120, dated Apr. 27, 2012.

International Search Report and Written Opinion, in Application PCT/US2011/042252, dated Apr. 6, 2011.

International Search Report and Written Opinion, in Application PCT/US2011/064989, dated Jun. 28, 2012.

International Search Report and Written Opinion, in Application PCT/US2011/026763, dated Nov. 14, 2011.

Supplemental Declaration Under 37 CFR 1.131 by inventors filed in U.S. Appl. No. 10/887,688, filed Sep. 14, 2009.

* cited by examiner

CONDUIT VASCULAR IMPLANT SEALING DEVICE FOR REDUCING ENDOLEAKS

PRIORITY

This application claims priority to U.S. Provisional Application No. 62/556,612 filed on Sep. 11, 2017, the disclosure of which is incorporated herein by reference in its entirely.

BACKGROUND

This patent document is directed to medical implants, and, more specifically, to conduit vascular implants and related methods.

Aneurysms of the aorta and principal arteries of the chest, abdomen and pelvis can progress, by expansion, to life-threatening rupture. Thrombus may develop within the aneurysm and cause embolic occlusion of arteries and ischemic organ injury. Clinical approach to treatment generally involves the insertion of a tubular graft that spans the extent of the aneurysmal portion of the vessel to exclude the aneurysm from the circulation by either surgical or transcatheter means, termed "endovascular aneurysm repair", or "EVAR". In either case, the success of the technique depends on effective sealing between the ends of the graft and the non-aneurysmal segments of the vessel proximal to and distal to the aneurysm to prevent leaking of blood flow into the aneurysm. The open surgical approach allows for complete suturing of the graft ends to the vessel and even excision of the aneurysm. However, transcatheter device insertion has supplanted the surgical approach for most aneurysms, owing to the clinical advantages of a minimally-invasive procedure with less morbidity and rapid recovery.

Devices for transcatheter insertion through the femoral artery and into the abdominal aorta for exclusion of an aneurysm are typically constructed, for example, of polymer fabric configured as a tube, with a metal alloy wire form or lattice attached at the ends or throughout the length of the resulting tube graft to provide axial and radial support and for fixation of the ends of the tube graft to the vessel. Such devices must be radially compressible to a profile that is capable of being inserted into the femoral artery and then expanded within the aorta to a size that matches that of the aorta and engages its inner wall for fixation and exclusion of the aneurysm. Shape memory alloy is widely utilized in these components.

Despite engagement and fixation of the ends of the transcatheter tube graft, leakage of blood into the aneurysm sac is relatively common and is termed "endoleak." Endoleak involves blood flow under normal hemodynamic pressure being conducted around the terminal edges of the conduit implant and into the aneurysm, thereby continuing to pressurize the aneurysm chamber and allowing possible progression to clinical aneurysm rupture. EVAR devices incorporate a number of features directed to limiting endoleak, including circumferential cuffs of additional graft material and stents for fixation and enhanced expansion of the graft ends against the inner wall of the vessel. Often, the vessel is susceptible to endoleak because of a short extent of mating inner surface of the vessel between the aneurysm and the origins of visceral arteries, such as the renal arteries, that cannot be covered and obstructed by the graft.

Existing methods and devices have shown variable effectiveness in limiting and/or preventing endoleak. Some of these devices are complex to manufacture or bulky in profile, which limits the ease of percutaneous delivery. Additionally, fabric or polymer layers have not been shown to promote biological integration of the prosthetic surface into the tissue environment of the vessel as well as do tissue membrane layers. Therefore, endoleak is a persistent problem for endovascular exclusion devices.

Accordingly, there is a need for a simple, reliable, low-profile device for minimizing endoleak associated with EVAR implants that is biocompatible with the native vascular intimal surface and promotes integration with the native tissue. In addition, other intravascular applications such as transcatheter heart valve implants may also benefit from devices that provide effective circumferential sealing between the implant and the native vascular site.

This patent document describes devices and methods that are intended to address issues discussed above and/or other issues.

SUMMARY

The summary of the disclosure is given to aid understanding of medical devices (such as vascular implants), and not with an intent to limit the disclosure or the invention. The present disclosure is directed to a person of ordinary skill in the art. It should be understood that various aspects and features of the disclosure may advantageously be used separately in some instances, or in combination with other aspects and features of the disclosure in other instances. Accordingly, variations and modifications may be made to the medical devices, the architectural structure, and their method of operation to achieve different effects.

In one aspect, a sealing device for use as a vascular implant comprises a frame having an inflow edge and an outflow edge relative to axial blood flow within a vessel, and a membrane layer coupled to the at least partial axial extent of the frame between the inflow edge and the outflow edge of the frame. At least a partial axial extent of the frame is configured to decrease in axial length when expanded from a radially compressed configuration to a radially expanded configuration. The membrane layer is coupled to the at least partial axial extent of the frame at one or more axially spaced connection points such that at least a portion of the membrane layer projects radially outward relative to the frame when the at least partial axial extent of the frame is in the radially-expanded configuration.

In some embodiments, the at least partial axial extent of the frame may be formed as a lattice structure. Optionally, the membrane layer may be coupled to the lattice structure at a plurality of axially-spaced and circumferentially-distributed connection points. Additionally and/or alternatively, the membrane layer may be coupled to the lattice structure by a plurality of sutures.

In one or more embodiments, the one or more connection points of the frame may include a plurality of circumferentially-distributed connection points proximate to the inflow edge of the at least partial axial extent of the frame.

In one or more embodiments, the one or more connection points of the frame may include a plurality of circumferentially-distributed connection points proximate to the outflow edge of the at least partial axial extent of the frame.

In certain other embodiments, the connection points of the frame may include one or more circumferentially-distributed connection points proximate to the outflow edge of the at least partial axial extent of the frame, one or more circumferentially-distributed connection points proximate to the inflow edge of the at least partial axial extent of the frame, and/or one or more intermediate connection points located axially between the connection points proximate the outflow edge and the connections points proximate the inflow edge. Optionally, the one or more intermediate connection points may be configured to enforce an inflow-angled fold in the membrane layer. Additionally, the one or more intermediate connection points may enforce an outflow-angled fold in the membrane layer. Furthermore, the one or more intermediate connection points may be configured to enforce both an inflow-angled and an outflow-angled fold in the membrane layer.

In some embodiments, the membrane layer may be formed of at least one of processed mammalian pericardium tissue, a biocompatible fabric, or a polymer material. The membrane layer may be formed of porcine and/or bovine pericardium tissue. Optionally, the membrane layer may be formed of a substantially dry tissue. In at least one embodiment, the sealing device may be in a radially-compressed condition and associated to a delivery system, and the delivery system associated with the sealing device may be provided in a sterile condition within an internally sterile package.

In certain embodiments, a circumferential extent of the membrane layer may exceed a circumferential extent of the frame. Alternatively, the circumferential extent of the membrane layer may not exceed a circumferential extent of the frame.

In at least one embodiment, the membrane layer may extend over an entire axial length of the frame. Alternatively, the membrane layer may extend over only a portion of an axial length of the frame. In yet another embodiment, the membrane layer may axially extend beyond at least one of the inflow edge or the outflow edge of the frame.

In some scenarios, the radially projecting portion of the membrane layer may be configured to contact an inner wall of the vessel to cause an impeding of blood flow over an outer surface of the sealing device.

In another aspect, a sealing device for use as a vascular implant is disclosed. The sealing device comprises a frame and a membrane layer. The frame is configured to have an at least partial expandable axial extent including a plurality of circumferentially distributed members configured to circumferentially separate from each other when expanded from a radially compressed configuration to a radially expanded configuration coupled to the at least partial expandable axial extent of the frame at a plurality of connection points. The membrane layer is configured to have at least a transverse curvilinear extent exceeding an underlying circumferential extent of the frame between connection points at an axial level of at least some of the connection points upon the frame.

In various embodiments, the connection points between the frame and the membrane layer may be circumferentially regularly spaced or circumferentially irregularly spaced.

In certain embodiments, the at least partial expandable axial extent of the frame may be formed as a lattice structure. Optionally, the membrane layer may be coupled to the lattice structure at a plurality of axially-spaced and circumferentially-distributed connection points by, for example, a plurality of sutures.

In some embodiments, the connection points of the frame may include a plurality of circumferentially-distributed connection points proximate to the inflow edge of the at least partial expandable axial extent of the frame. Additionally and/or alternatively, the one or more connection points of the frame may include a plurality of circumferentially-distributed connection points proximate to the outflow edge of the at least partial expandable axial extent of the frame. Optionally, the connection points of the frame may include one or more circumferentially-distributed connection points proximate to the outflow edge of the axial extent of the frame, one or more circumferentially-distributed connection points proximate to the inflow edge of the axial extent of the frame, and/or one or more intermediate connection points located axially between the connection points proximate the outflow edge and the connection points proximate the inflow edge.

In at least one embodiment, wherein the membrane layer may be formed of processed mammalian pericardium tissue (e.g., bovine or porcine), a biocompatible fabric, and/or a polymer material.

Optionally, the membrane layer may be formed of a substantially dry tissue. In at least one embodiment, the sealing device may be in a radially-compressed condition and associated to a delivery system, and the delivery system associated with the sealing device may be provided in a sterile condition within an internally sterile package.

In at least one embodiment, the membrane layer may extend over an entire axial length of the frame. Alternatively, the membrane layer may extend over only a portion of an axial length of the frame. In yet another embodiment, the membrane layer may axially extend beyond at least one of the inflow edge or the outflow edge of the frame. In some embodiments, the membrane layer may extend over an entire circumferential length of the frame and/or over only a portion of a circumferential length of the frame.

In some scenarios, the radially projecting portion of the membrane layer may be configured to contact an inner wall of the vessel to cause an impeding of blood flow over an outer surface of the sealing device.

Additionally and/or alternatively, the radially projecting portion of the membrane layer may be configured to contact an inner wall of the vessel to cause an impeding of blood flow over an outer surface of the sealing device.

In some other scenarios, one or more of the connections at the connection points may enforce a radially outwardly angled direction upon the membrane layer adjacent the connection points.

In various embodiments, two or more portions of the membrane layer may be connected at connection points independent of the connections to the frame and/or may form one of a linear or curvilinear seam of at least two points.

DETAILED DESCRIPTION

The following description is made for the purpose of illustrating the general principles of the present system and method and is not meant to limit the inventive concepts claimed in this document. Further, particular features described in this document can be used in combination with other described features in each of the various possible combinations and permutations.

Unless otherwise specifically defined in this document, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified. Unless defined otherwise, all technical and scientific terms used herein have the same meanings as commonly understood by one of ordinary skill in the art. All publications mentioned in this document are incorporated by reference. Nothing in this document is to be construed as an admission that the embodiments described in this document are not entitled to antedate such disclosure by virtue of prior invention. As used herein, the term "comprising" means "including, but not limited to". Additionally, use the term "couple", "coupled", or "coupled to" may imply that two or more elements may be directly connected or may be indirectly coupled through one or more intervening elements.

In this document, position-identifying terms such as "inflow", "outflow", "vertical", "horizontal", "front", "rear", "top", and "bottom" are not intended to limit the invention to a particular direction or orientation, but instead are only intended to denote relative positions, or positions corresponding to directions shown when a vascular implant is oriented as shown in the Figures. Accordingly, the provided orienting descriptions of the device do not limit its use to the inflow end of an exclusion graft or device; the device may also be used at the outflow end of an exclusion graft or device.

Figure 1:
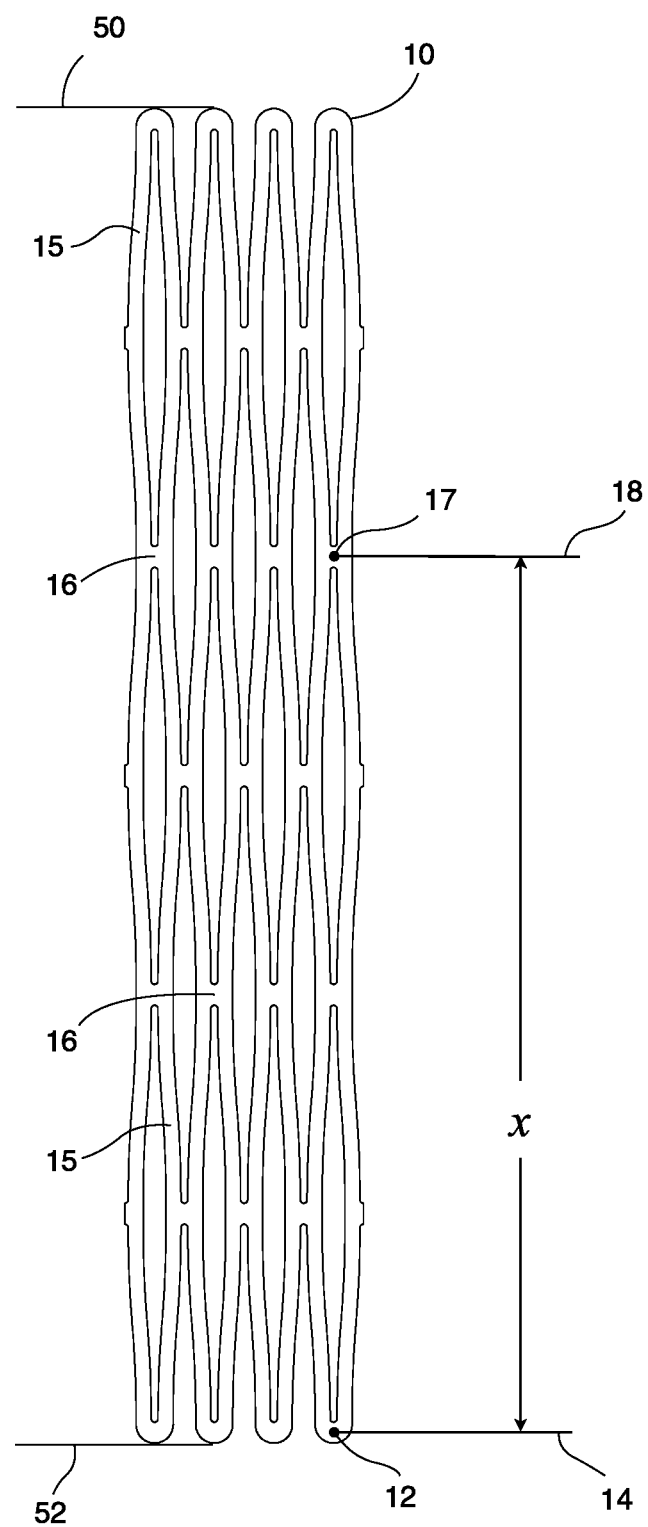
FIG. 1 illustrates a radially-compressed cylindrical lattice frame for a vascular implant, according to an embodiment.

Referring to FIG. 1, a radially-compressed (or radially-crimped) cylindrical lattice frame 10 for use in, e.g., a vascular implant, is illustrated. For clarity of illustration, only the foreground portion of cylindrical lattice frame 10 is shown in FIG. 1, with the background portion omitted. Frame 10 may be used in conjunction with a transcatheter tube graft implant. Accordingly, frame 10 may be formed of any appropriate biocompatible material, such as stainless steel, gold, titanium, cobalt-chromium alloy, tantalum alloy, nitinol, one or more biocompatible polymers, etc.

Frame 10 includes an inflow edge 50 and an outflow edge 52 relative to axial blood flow within a vessel in which the implant is placed. Frame 10 may be formed by a plurality of arms 15 interconnected by a plurality of circumferentially-distributed connection nodes 16 to form a cylindrical lattice structure. The lattice structure of frame 10 may be originally fabricated or cut in the configuration shown in FIG. 1. However, it is to be understood that frame 10 may be formed by any appropriate method, and is not limited by the lattice structure illustrated in FIG. 1.

Figure 2:
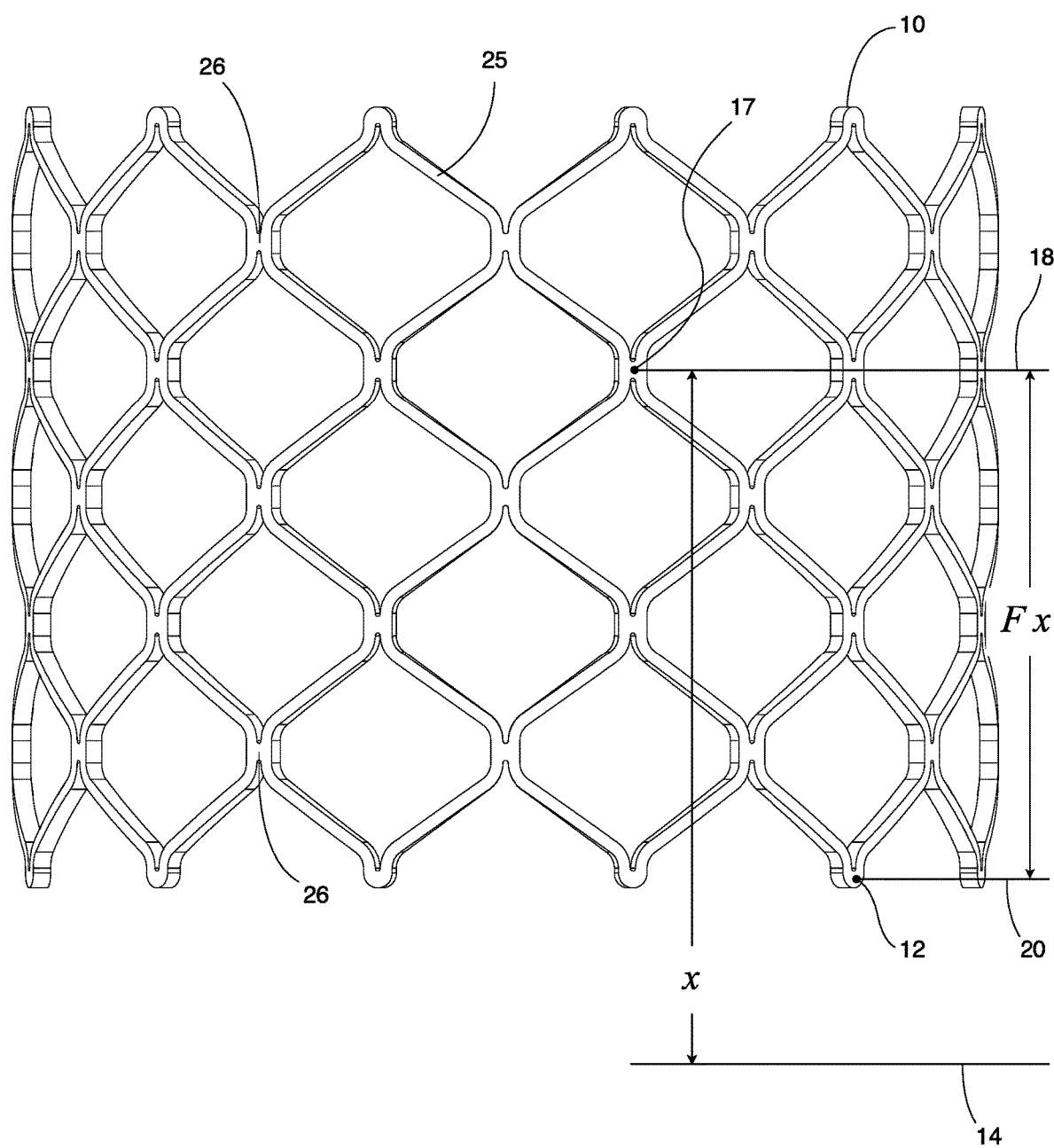
FIG. 2 illustrates an expanded cylindrical lattice frame for a vascular implant, according to an embodiment.

As shown in FIG. 1, when frame 10 is in a radially-compressed state, an axial distance x exists between two random (but approximately circumferentially-aligned) node points 12, 17 having respective baselines 14, 18. However, when the cylindrical lattice structure of frame 10 is radially expanded, as illustrated in FIG. 2, the overall axial length of frame 10 between points 12 and 17 shortens. For example, in a radially-expanded state, the axial distance between node points 12, 17 becomes a distance Fx between baselines 20, 18, with distance Fx being shorter than distance x between baselines 14, 18. Thus, when used in a vascular implant, radial expansion of frame 10 in the direction of the vessel walls leads to axial compression of frame 10.

Figure 3:
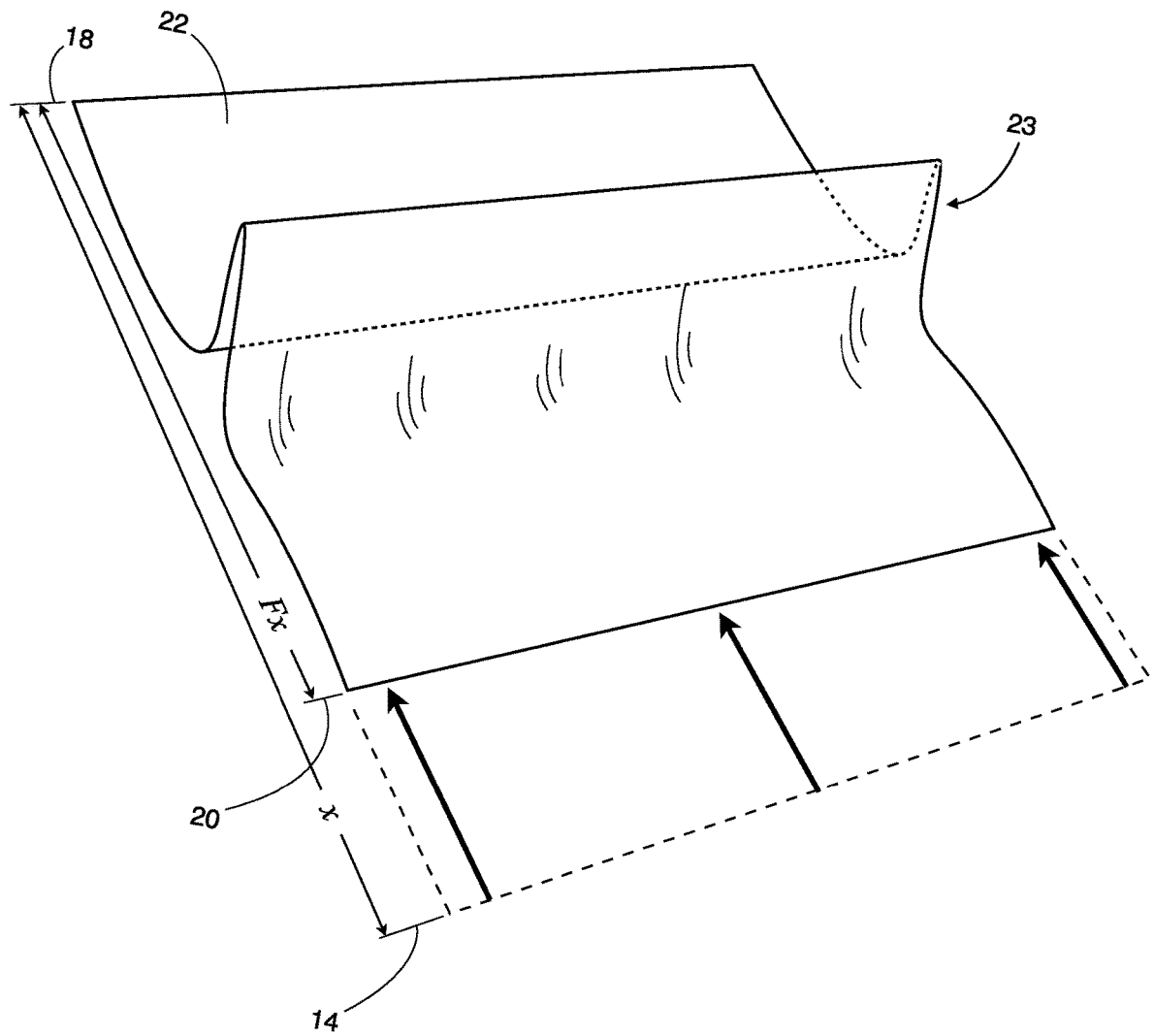
FIG. 3 illustrates a membrane layer for a vascular implant in an axially-shortened state, according to an embodiment.

Referring now to FIG. 3, a membrane layer 22 configured for use in conjunction with frame 10 is illustrated. Indicated by arrows, as membrane layer 22 axially shortens from baseline 14 to baseline 20, a redundant portion 23 of membrane layer 22 is then projected out of plane, corresponding to the radially-outward direction from the underlying frame 10. This redundant material 23 increases the membrane layer local material density which occupies the space between the frame 10 and the inner surface of the vascular wall, adding to the sealing function of the membrane layer 22. While shown (for ease of illustration) as a substantially flat sheet in FIG. 3, it is to be understood that membrane layer 22 may be cylindrically wrapped or otherwise formed around frame 10 to form a cylindrical, tube-like structure. As will be discussed further below, in accordance with some embodiments, membrane layer 22 may be formed as an axially-complete layer over the entire axial length of frame 10. However, in accordance with other embodiments, membrane layer 22 may be formed as an axially-incomplete layer of the length of frame 10. Furthermore, in some embodiments, the axial length of membrane layer 22 may exceed the axial length of frame 10. Additionally, in some embodiments, the circumferential extent of the membrane layer 22 may not exceed the circumferential extent of underlying frame 10, while in other embodiments, the circumferential extent of the membrane layer 22 does exceed the circumferential extent of underlying frame 10.

Membrane layer 22 may be formed of any appropriate biocompatible material, such as, for example, processed mammalian pericardium tissue (e.g., porcine or bovine pericardium), a biocompatible fabric, a polymer material (e.g., polytetrafluoroethylene (PTFE)), etc.

Figure 4:
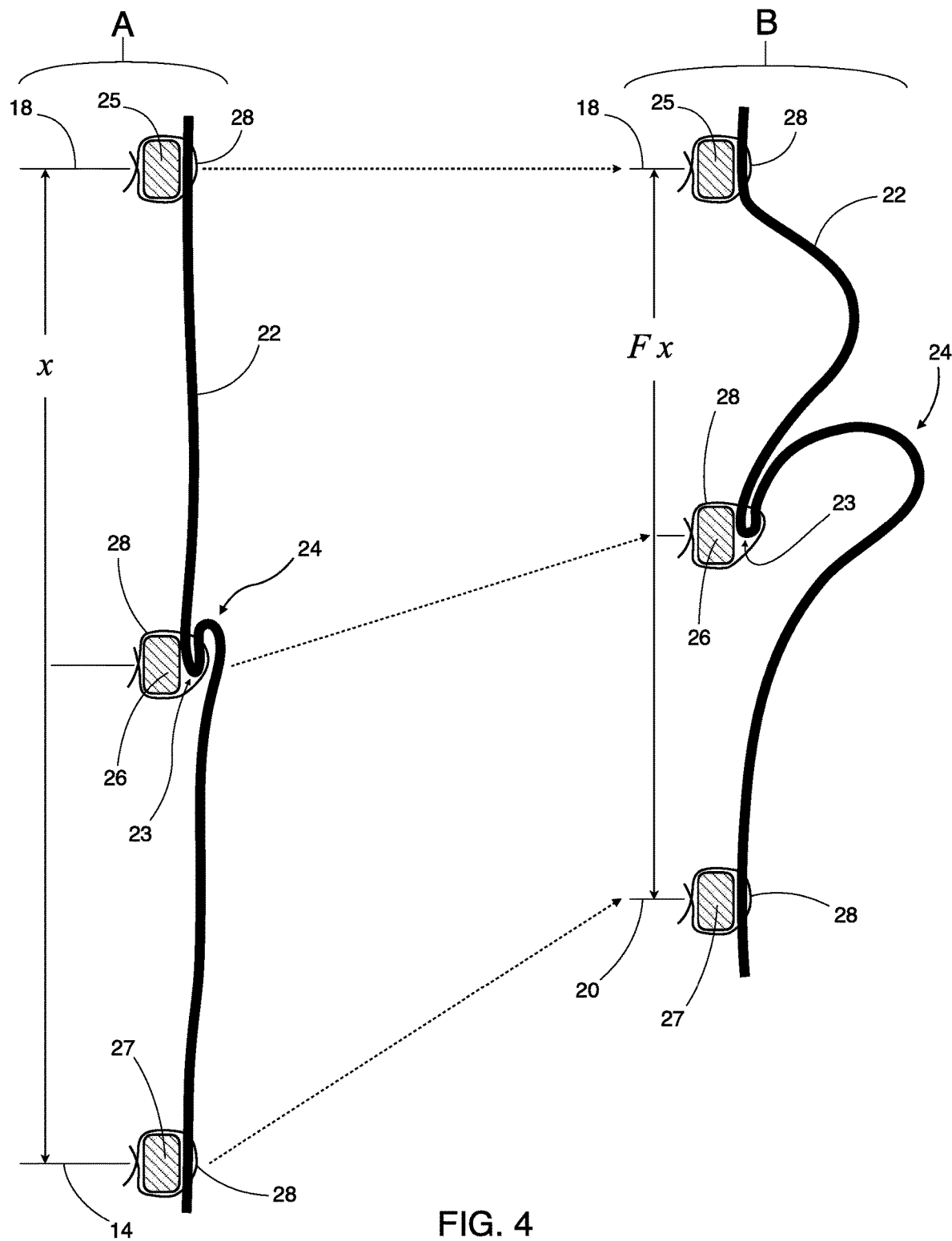
FIG. 4 illustrates a longitudinal cross-sectional view of suture attachment of a membrane layer to a lattice frame for a vascular implant in both a radially-compressed configuration and a radially-expanded configuration, according to an embodiment.

Membrane layer 22 may be coupled at least partially to an outer surface frame 10 by any appropriate method. For example, FIG. 4 shows a cross-sectional view of a single side of the membrane layer and frame members at points of interconnection. As shown in FIG. 4, portions of membrane layer 22 are coupled to a plurality of circumferentially-distributed and axially-separated connection points 25, 26, 27 of frame 10 through respective sutures 28. In one aspect of the present disclosure, a fold 24 may be created during the coupling of membrane layer 22 to an intermediate connection point(s) 26 that is axially between the inflow-side connection point(s) 25 and the outflow-side connection point(s) 27. For example, referring to configuration "A" of FIG. 4, which illustrates the membrane layer 22 coupled to frame 10 when frame 10 is in the radially-compressed configuration shown in FIG. 1, two sides of fold 23 at the base of projecting fold 24 are coupled to the intermediate connection point(s) 26 by a suture 28 such that the fold 24 is effectively biased to one side of the intermediate connection point(s) 26. When frame 10 is radially expanded (as shown in FIG. 2), the accompanying axial compression of at least a portion of frame 10 from an axial distance x to an axial distance Fx causes the coupled membrane layer 22 to similarly compress. Due to two sides of fold 23 being coupled to the intermediate connection point(s) 26, such axial compression of frame 10 to axial distance Fx also causes membrane layer 22 to radially project outward, away from frame 10, as is shown in configuration "B" of FIG. 4. As will be described further below, this radially-outward projection of membrane layer 22 at fold 24 may provide for improved sealing between the transcatheter tube graft implant and a vessel to mitigate endoleaks around the periphery of the implant.

As shown in FIG. 4, membrane layer 22 not only projects radially outward away from frame 10, but also projects at least partially upward (e.g., toward an inflow end relative to blood flow through a vessel). This upward projection is due to the orientation in which the two sides of membrane layer 22 are overlapped when coupled to intermediate connection point(s) 26. Thus, it is also possible for the membrane layer 22 to be overlapped in the direction opposite of that shown in FIG. 4, which would cause membrane layer 22 to project both radially outward and downward away from frame 10. Furthermore, while not shown, membrane layer 22 may be overlapped and connected to connection point(s) 26 such that the fold 24 may be expanded to project both toward an upward (inflow) end and a downward (outflow) end of the frame. It is to be understood that similar folds in the membrane layer may be configured at other and possibly multiple points of connection or between points of connection by sutures or other means not connecting membrane layer 22 to frame 10.

Figure 5:
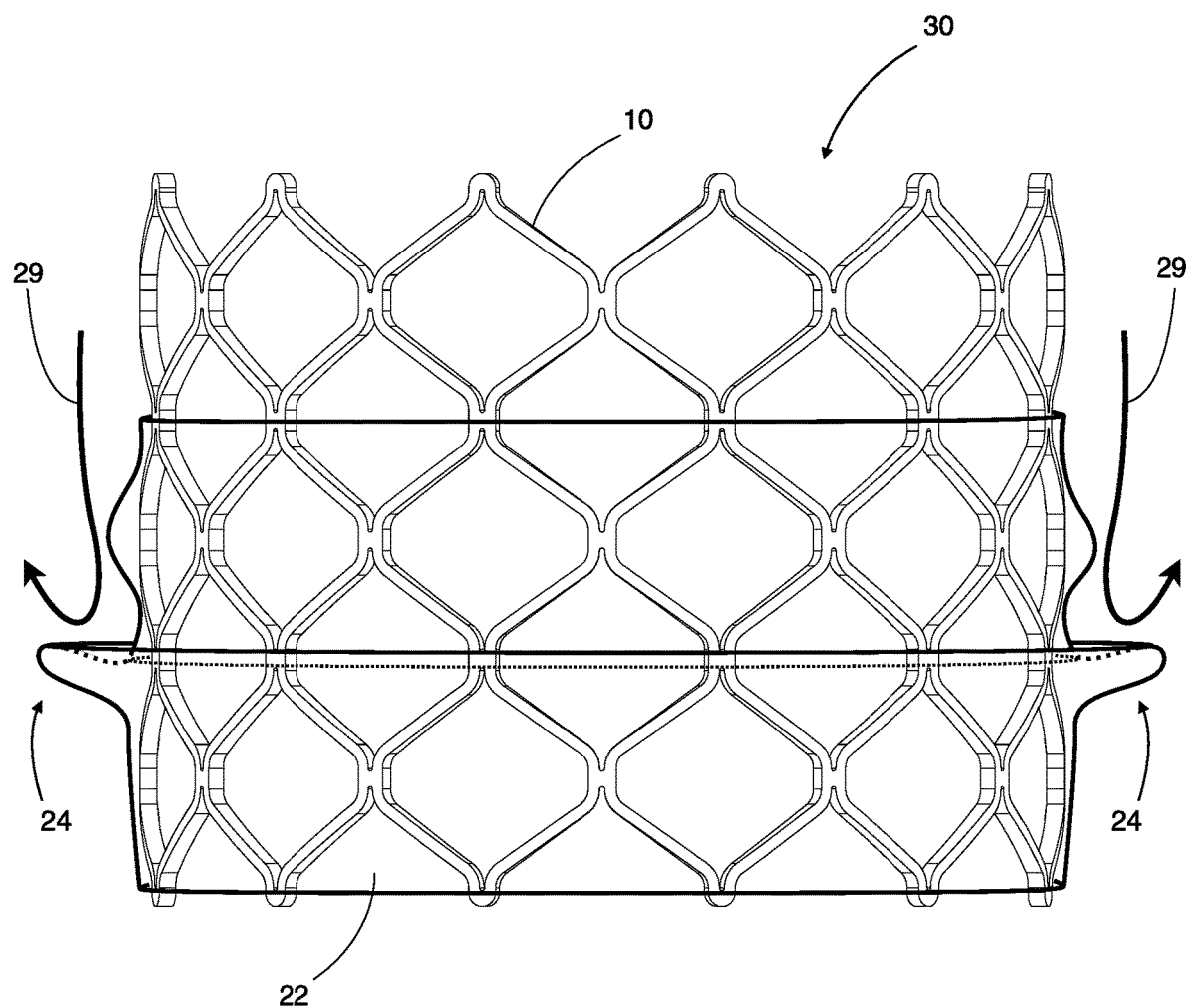
FIG. 5 illustrates a side elevation view of an axially-shortened membrane layer on a radially-expanded lattice frame for a vascular implant, according to an embodiment.

Referring to FIG. 5, a simplified view of an implant 30 in accordance with an aspect of the disclosure is illustrated. For clarity, sutures or other interconnection means between the membrane layer 22 and frame 10 are omitted from FIG. 5. As described above with respect to FIG. 4, when frame 10 is radially expanded (and axially compressed), the surrounded membrane layer 22 is also axially compressed, resulting in the fold 24 projecting radially outward around the entire circumference of frame 10. The radial projection formed by fold 24 may act as a seal between the membrane layer 22 and the vessel walls (not shown) when implant 30 is placed in a desired location, with fold 24 of membrane layer 22 blocking some or all of the blood flowing around the periphery of implant 30, thereby mitigating endoleaks, as indicated by arrows 29.

Figure 6:
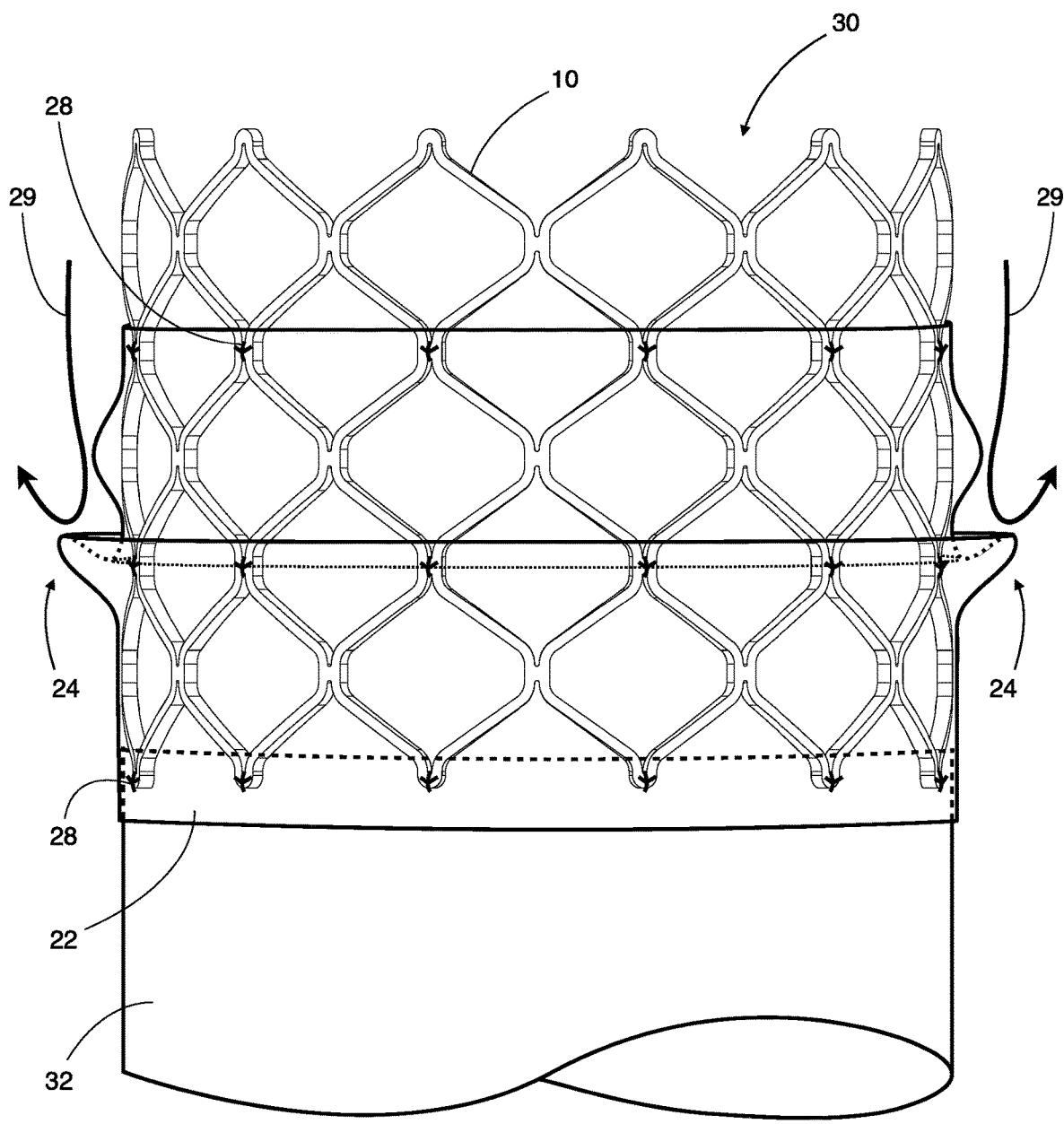
FIG. 6 illustrates a side elevation view of an axially-shortened membrane layer coupled to a radially-expanded lattice frame, according to an embodiment.

As shown in FIG. 6, implant 30 may include a plurality of sutures 28 utilized to couple the membrane layer to a plurality of connection points of the frame 10. In addition, a tube graft 32 may be coupled to the outflow side of frame 10. An inflow side of tube graft 32 may overlap with an outflow side of membrane layer 22, with the inflow side of tube graft 32 configured to share the sutures 28 coupling membrane layer 22 to frame 10. Once again, while sutures 28 are illustrated, it is to be understood that any appropriate connection means between the membrane layer, tube graft, and frame may be utilized.

Sutures (or other connectors) 28 coupling membrane layer 22 to frame 10 need not lie directly upon an inflow or outflow edge of frame 10, as only axial separation between the circumferential connection points 25, 26, 27 (shown in FIG. 4) is needed if there is axial shortening of the corresponding circumferentially-complete underlying portion of the frame 10 upon radially expansion of the frame 10. Further, the biocompatible membrane layer 22 need not terminate in either inflow or outflow ends of the axial extent of the frame 10. For example, in one aspect of the present disclosure, the membrane layer 22 may extend at least to and be interconnected along (1) an outflow end of the axial extent corresponding to the outflow edge of the frame 10 and (2) an inflow end of the axial extent between the inflow and outflow edges of the frame 10 approximating the axially mid portion of the frame 10, such as that which is shown in FIGS. 5-6.

Figure 7:
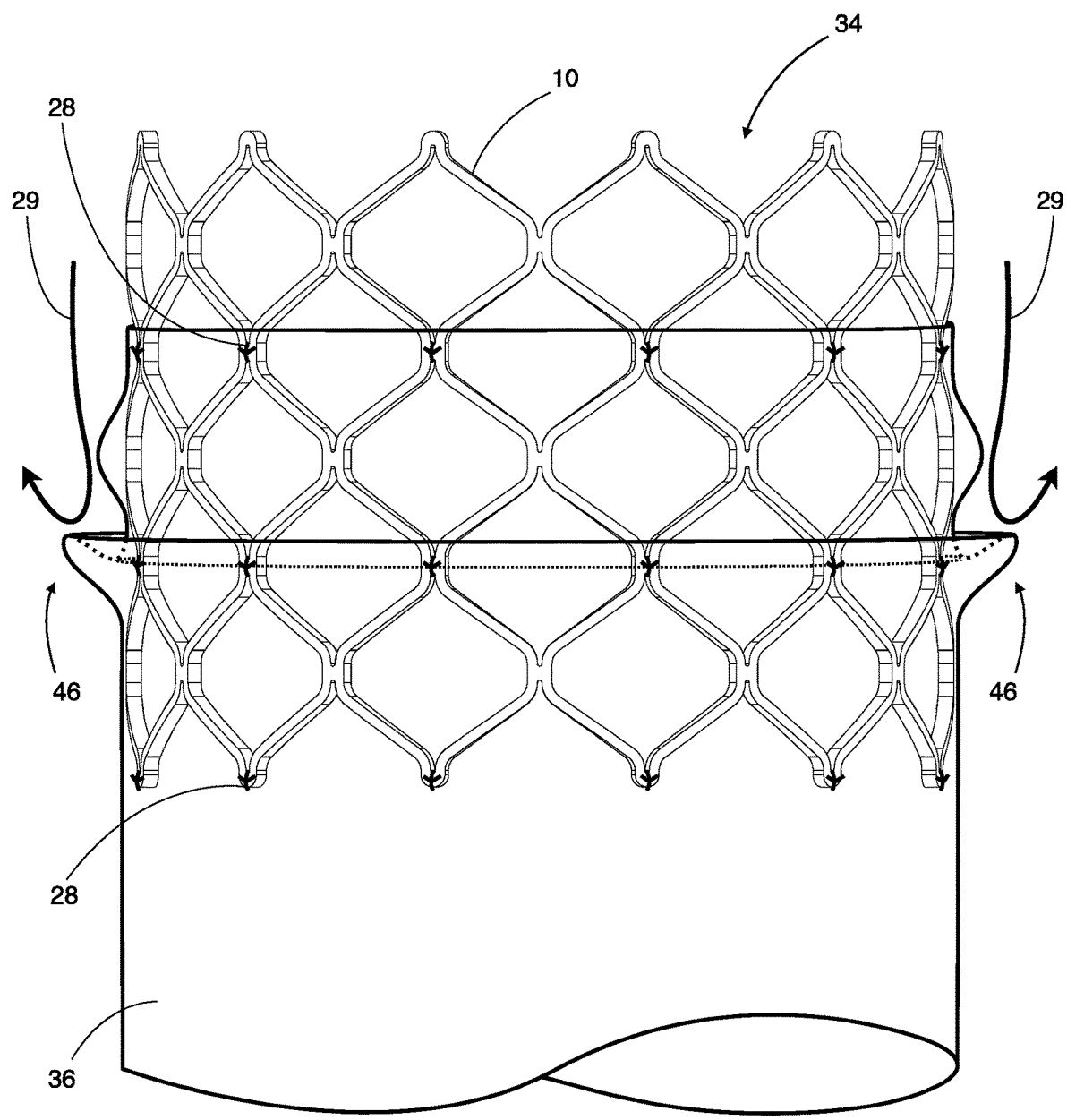
FIG. 7 illustrates a side elevation view of an axially-shortened membrane layer coupled to a radially-expanded lattice frame, according to another embodiment.
Figure 8:
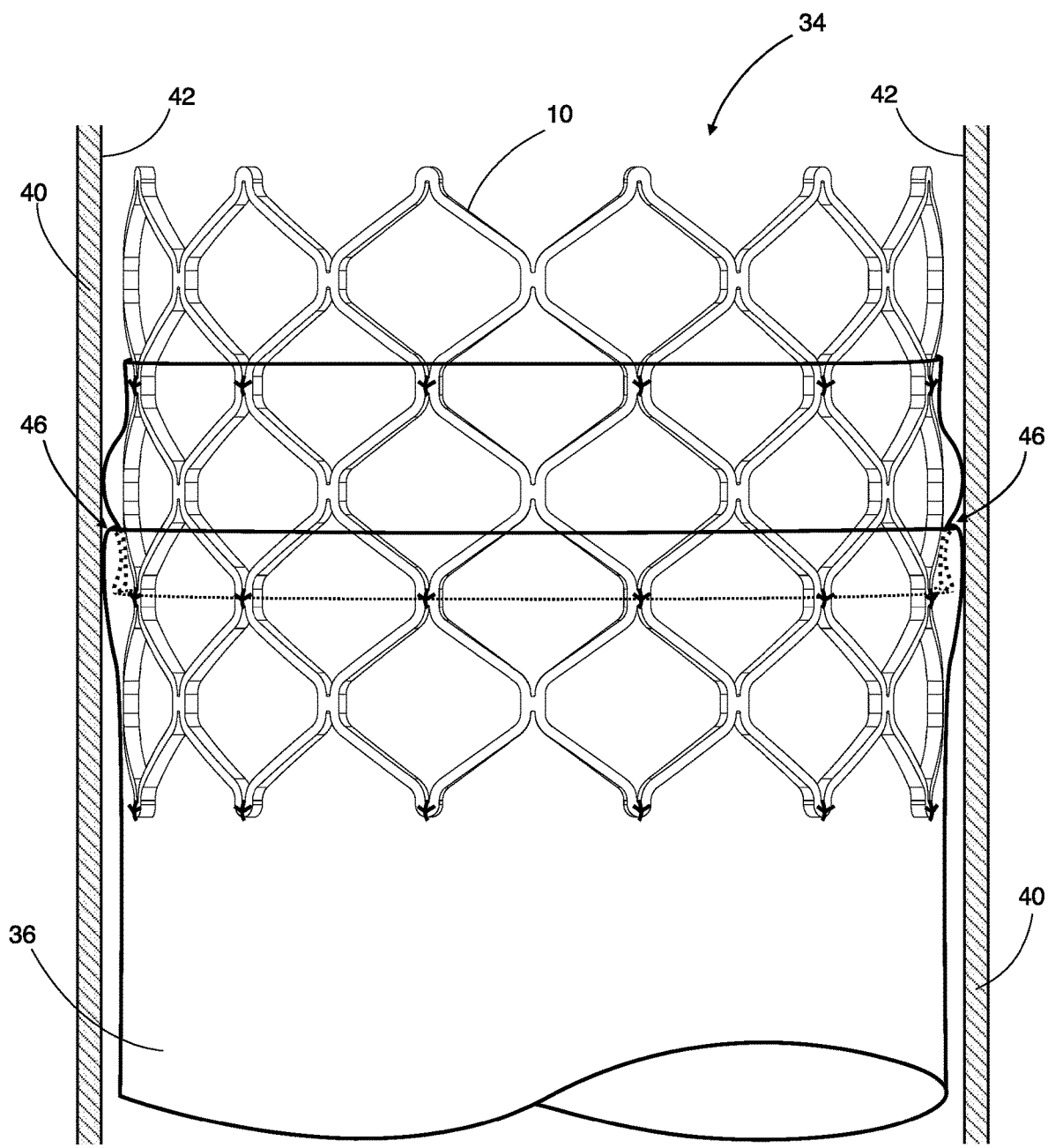
FIG. 8 illustrates a side elevation view of an axially-shortened membrane layer coupled to a radially expanded lattice frame and deployed within a vessel, according to an embodiment.

Referring now to FIGS. 7-8, an implant 34 in accordance with another aspect of the present disclosure is illustrated. Unlike the membrane layer 22 described above with respect to FIG. 6, which formed a sealing device separate from tube graft 32, implant 34 includes a tube graft 36 in which the sealing device is integrally formed on an inflow end of tube graft 36. Specifically, a portion of tube graft 36 is disposed at least partially around a frame 10 and coupled to frame 10 via sutures 28 in a manner similar to that described above with respect to FIG. 4. When frame 10 is radially expanded (as shown in FIG. 7), the portion of tube graft 36 surrounding frame 10 axially compresses, thereby causing one or more folds 46 to project radially outward, allowing this radially projecting portion of tube graft 36 to form a seal against some or all blood flowing around the periphery of implant 34 as indicated by arrows 29.

FIG. 8 illustrates the implant 34 as described above with respect to FIG. 7 deployed within, e.g., a vessel portion 40 shown in cross-section. As is shown, the radially projecting folds 46 of tube graft 36 are configured to at least partially compress against the inner walls 42 of vessel 40 when frame 10 is radially expanded, thereby providing an effective barrier seal against endoleak or other fluid flow past the outer periphery of implant. In the embodiment shown in FIG. 8, folds 46 are shown as being compressed against the inner walls 42 and angled toward the inflow end of the frame. However, as described above, implant 34 could alternatively be configured such that folds 46 are compressed against inner walls 42 and angled toward the outflow end of the frame.

While FIG. 2 shows the entirety of frame 10 being axially compressed when in a radially-expanded state, it is to be understood that, in some embodiments, only a certain axial extent of frame 10 may be axially compressed when in a radially-expanded state. That is, in some embodiments, portions of frame 10 may be capable of remaining substantially constant in axial length, even when frame 10 is expanded radially, while other portions along an axial extent of the frame 10 may axially compress.

Figure 9:
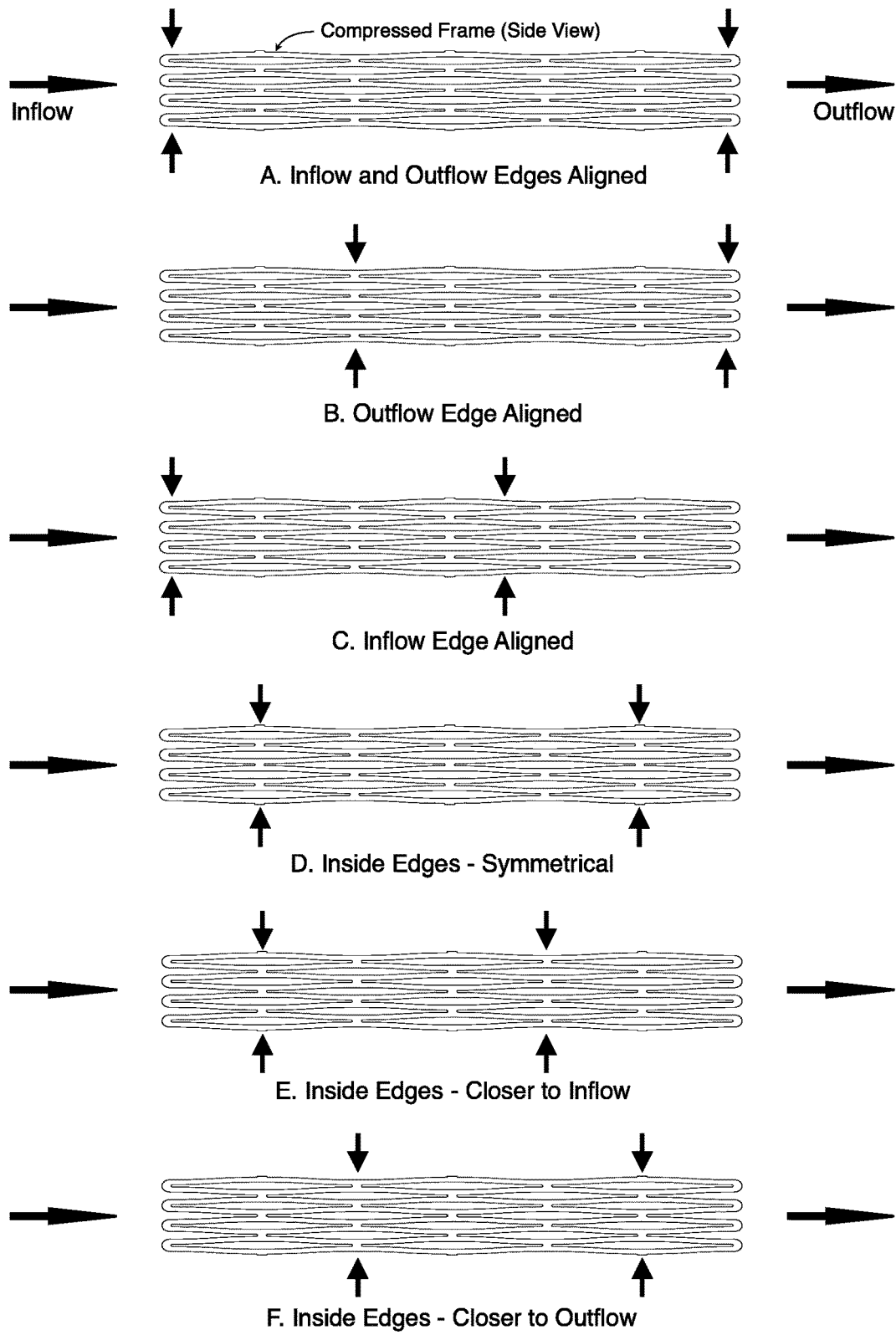
FIG. 9 illustrates a plurality of side elevation views of variations in axial position of attachment points along a radially compressed lattice frame, according to various embodiments.

For example, referring to FIG. 9, a plurality of example variations of axial membrane attachment points on a radially-compressed frame are shown, with the axial membrane attachment points being indicated by inwardly-pointed arrows. As is shown in FIG. 9, the axial membrane attachment points can be at numerous different locations along the frame between the inflow and outflow edges, including at locations inset from the inflow edge, outflow edge, or both. In variations in which the axial extent of the membrane attachment points does not extend entirely to the inflow and outflow edges (e.g., variations B-F shown in FIG. 9), the portions of the frame located outside of the axial extent between the membrane attachment points do not necessarily need to axially shorten during radial expansion in order to achieve a desired radial projection in the membrane. Accordingly, these portions of the frame located outside of the axial extent between the membrane attachment points may be configured differently than the portions within the axial extent such that all or some of the frame portions located outside of the axial extent do not compress/shorten with radial expansion.

Figure 10:
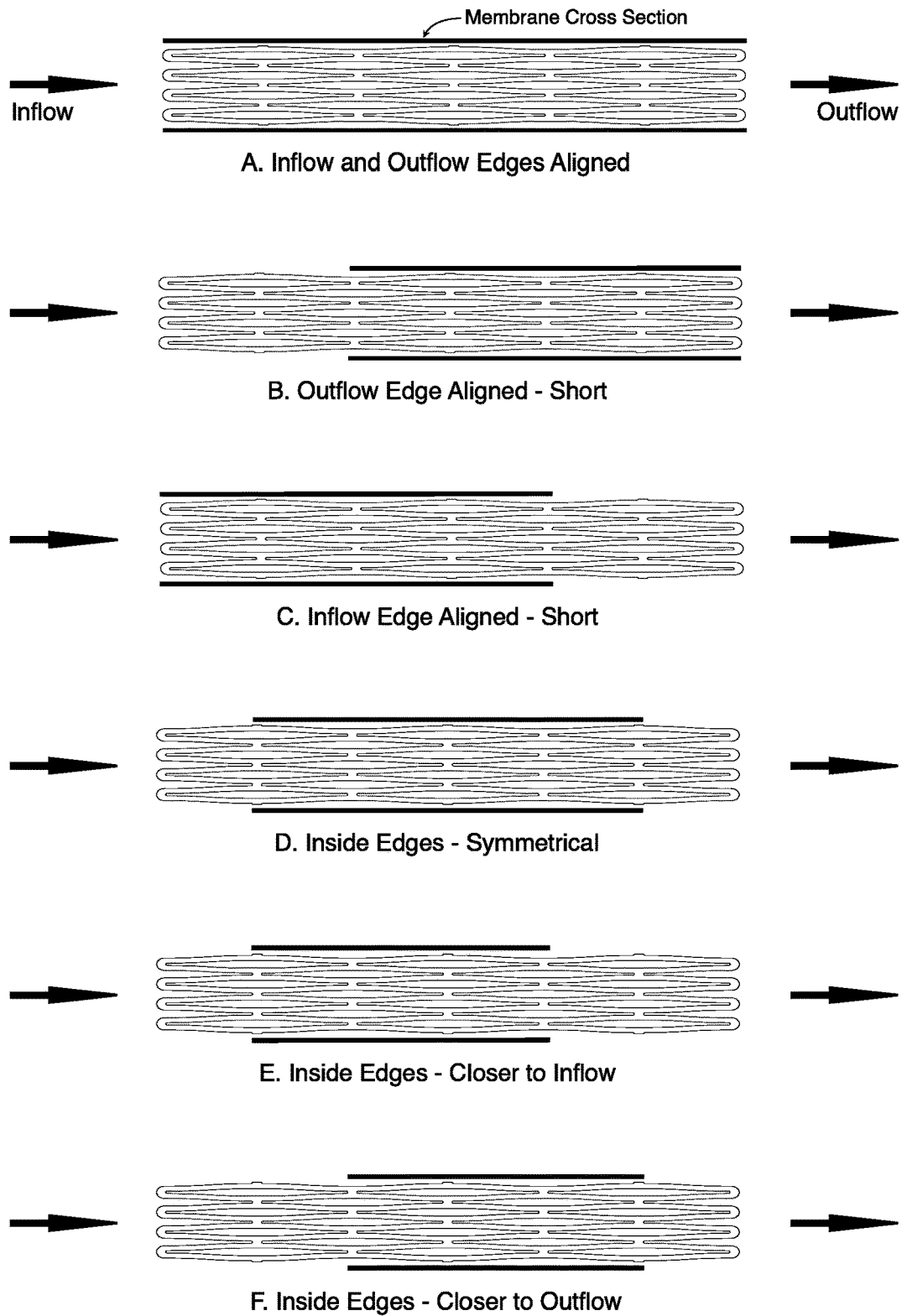
FIG. 10 illustrates a plurality of side elevation views of variations in axial position of membranes along a radially compressed lattice frame, according to various embodiments.
Figure 11:
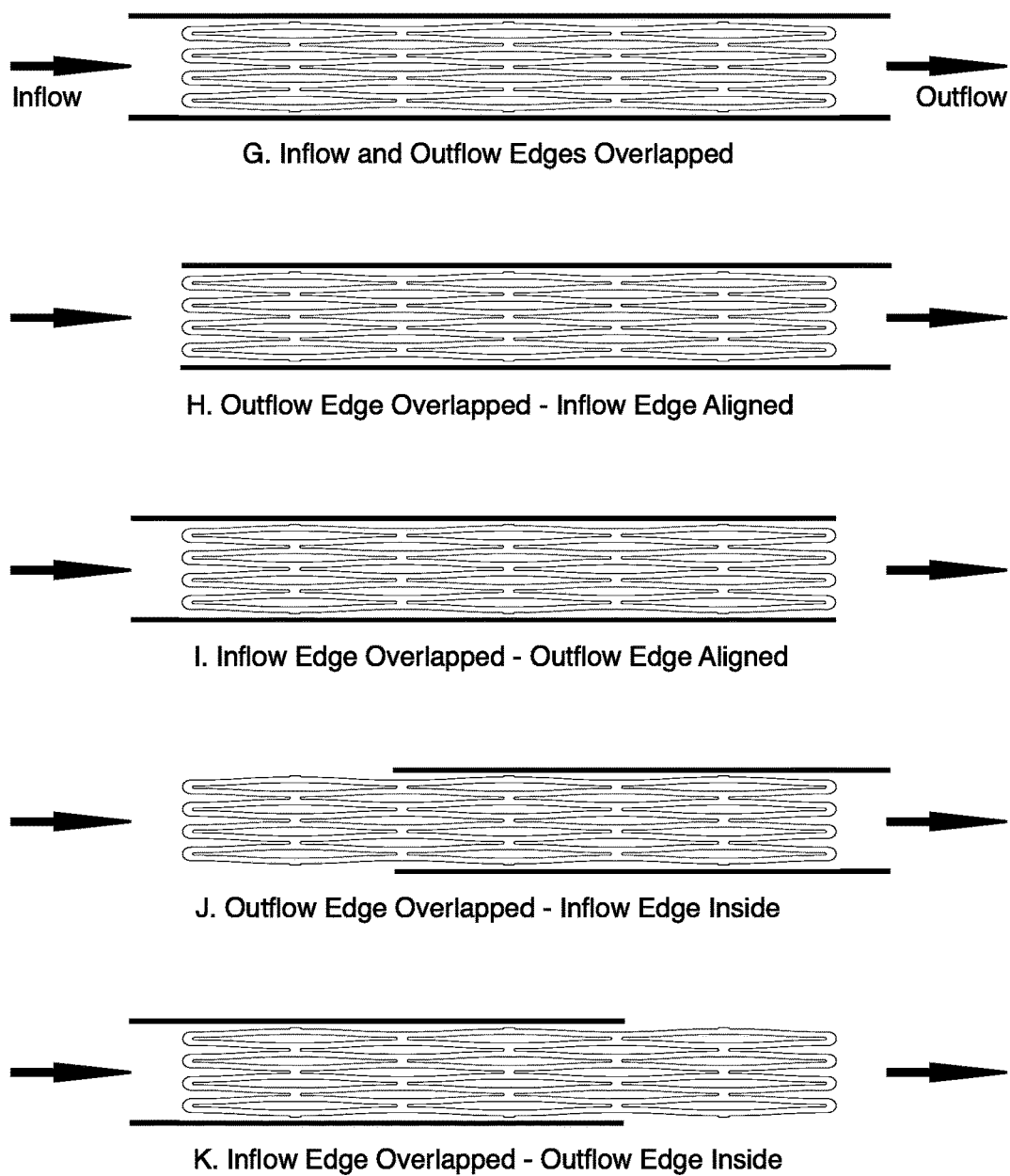
FIG. 11 illustrates a plurality of side elevation views of variations in axial position of membranes along a radially compressed lattice frame, according to various embodiments.

Similarly, referring to FIGS. 10-11, a plurality of example variations in the axial extent and position of the membrane relative to a radially-compressed frame are illustrated. As discussed above with respect to FIG. 9, the axial membrane attachment points can be at numerous different locations along the frame between the inflow and outflow edges, including at locations inset from the inflow edge, outflow edge, or both. Accordingly, the membrane itself may also axially extend along less than the entirety of the frame (e.g., variations B-F shown in FIG. 10), dependent upon the axial position of the attachment points. Additionally and/or alternatively, the membrane may extend beyond the inflow and/or outflow edges of the frame (e.g., variations G-K shown in FIG. 11). In such configurations, the membrane portions located between axial membrane attachment points may axially shorten in conjunction with radial expansion of the frame, while the membrane portions located outside of the axial membrane attachment points (and/or outside of the frame itself) may not change in axial length.

Figure 12:
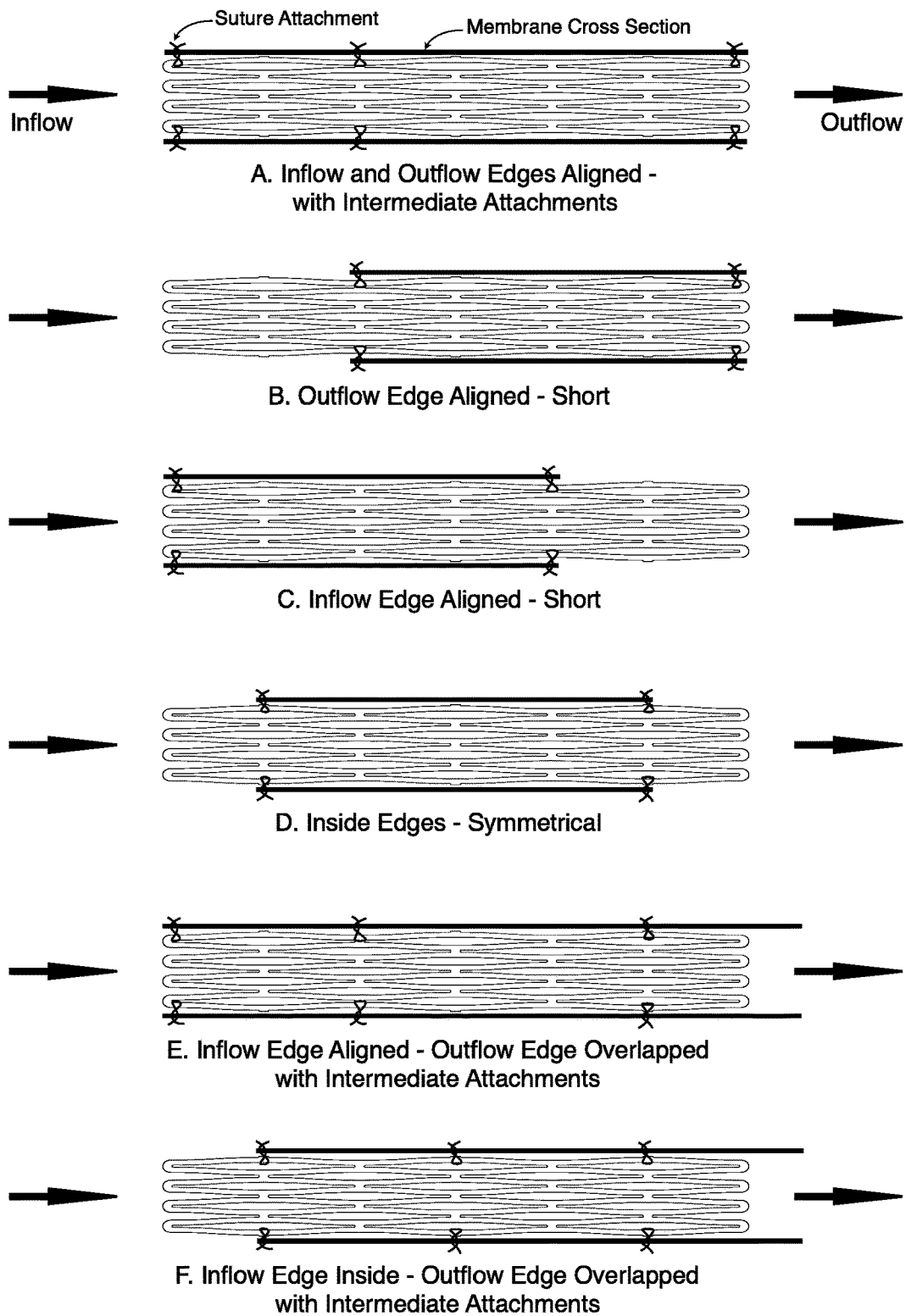
FIG. 12 illustrates a plurality of side elevation views of variations in axial position of membranes along a radially compressed lattice frame showing variations of attachments of the membrane to the frame, according to various embodiments.

Referring to FIG. 12, a plurality of example variations of suture attachment schemes for the attachment of the membrane to the radially-compressed frame are shown. It is to be understood that the suture attachments schemes shown in FIG. 12 are not limiting, as different attachment schemes are also possible. In some variations (e.g., variations B-D), suture attachments are placed at a pair of axial locations along the axial length of the membrane. However, in other variations (e.g., variations A, E, F), intermediate suture attachments may also be included along the axial length of the membrane. In accordance with the depiction of the cross-sectional view of the generally cylindrically disposed membrane layer, it is to be understood that the axial position of suture attachments is indicated in FIG. 12, but at each indicated axial position the attachments are circumferentially distributed.

Figure 13:
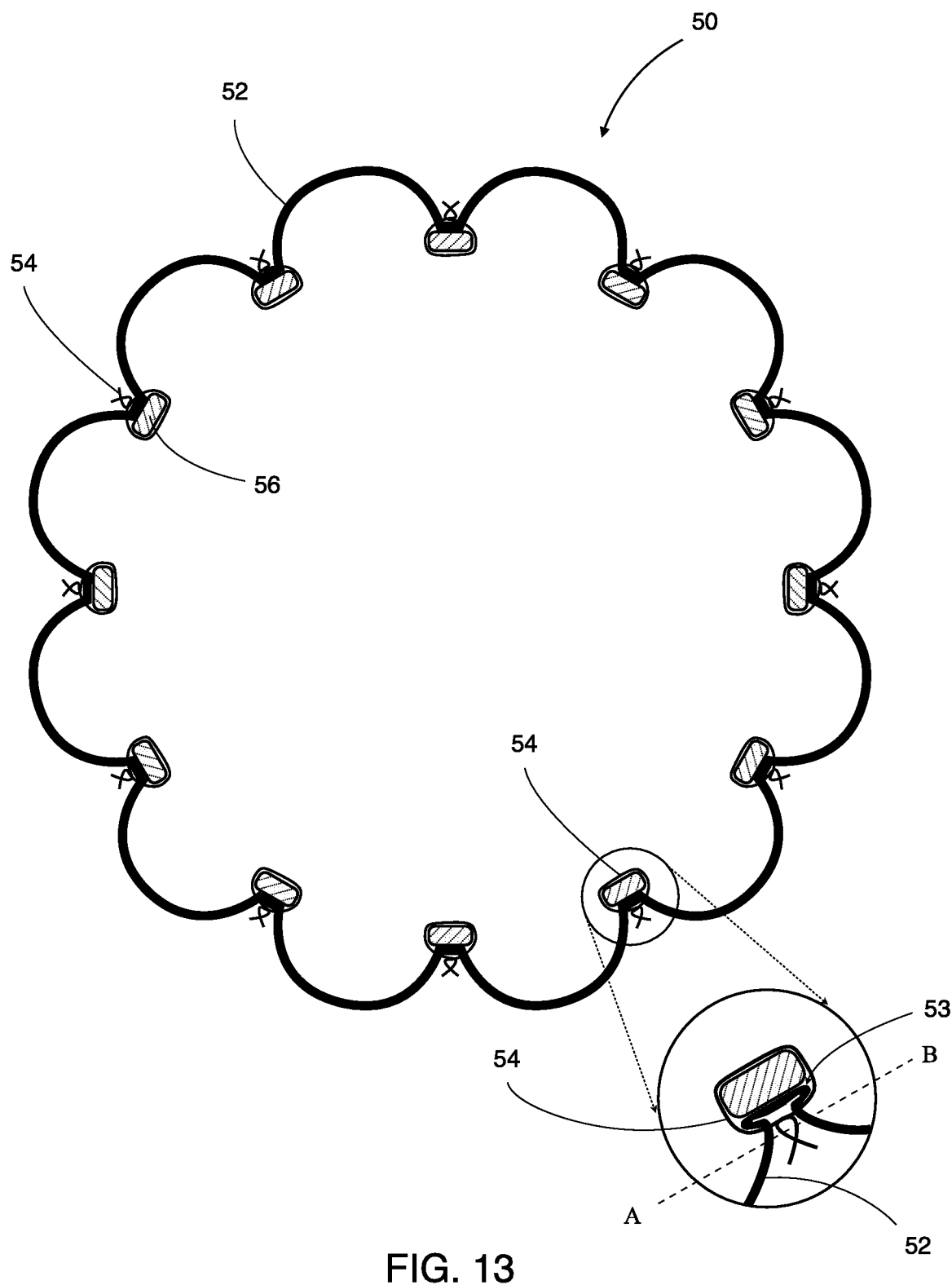
FIG. 13 illustrates a transverse cross section of a vascular implant, according to another embodiment.
Figure 14:
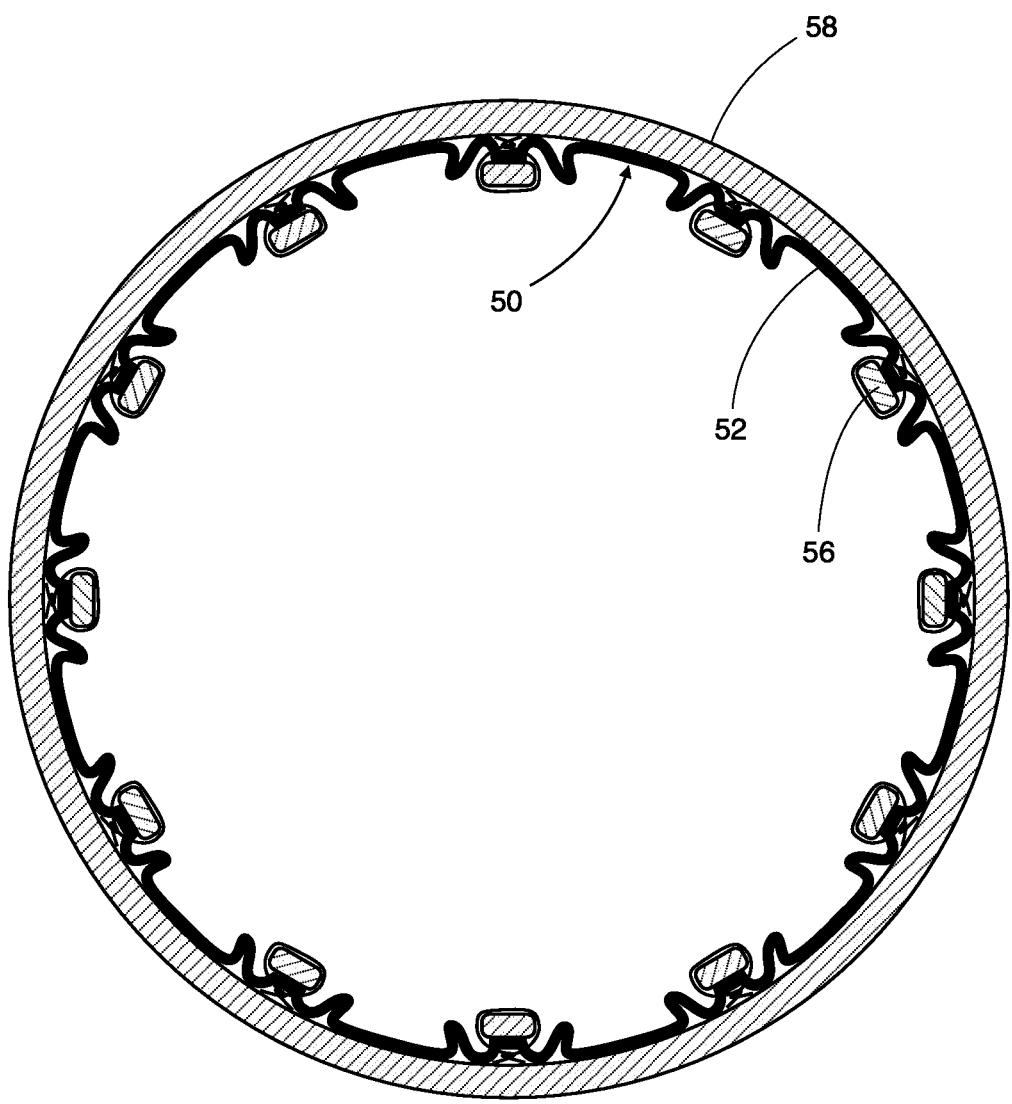
FIG. 14 illustrates a transverse cross section of the vascular implant of FIG. 13 expanded within a vessel.

Next, referring to FIGS. 13-14, an implant 50 in accordance with another aspect of the disclosure is illustrated. Specifically, FIG. 13 shows a transverse cross-sectional view of implant 50 having a circumferentially-redundant membrane 52 coupled to an expanded frame 56 along a plurality of attachment points by a plurality of sutures 54 such that the transverse curvilinear extent of the membrane spanning the circumferential separation between two or more points of attachment to the frame exceeds that circumference separation. While frame 56 is shown in an expanded state, it is to be understood that frame 56 may be radially compressed, similar to frame 10 described above. Membrane 52 is sized so as to be circumferentially larger than radially-expanded frame 56, thereby causing the portions of membrane 52 located between the plurality of attachment points along frame 56 to bulge outward, even when frame 56 is radially expanded. As shown in the inset figure of FIG. 13, each radially outward transverse bulge in the membrane may be enhanced by biasing the membrane to the outward radial direction at the points of attachment by the specific means of attachment. In the example shown in the inset figure, the suture attachment 54 is configured to capture and enforce folds 53 in the membrane such that an outward bias in the curve of the bulge is developed. The membrane material may be configured by thickness and stiffness, for example, to create firmness of the bulges suitable to the sealing function. In another biasing mechanism indicated in the inset figure, the two sides of the membrane departing from the point of attachment may be connected at line A-B to each other as by suturing either adjacent the point of attachment alone or along an axial length to form at least a partial seam. Line A-B and points of membrane connection aligned to it may be radially or axially displaced from the underlying frame by an arbitrary distance. Single sutures or seams of suture or other means of connection may be used to create other or multiple folds of arbitrary biasing direction at any place in the membrane layer.

As shown in FIG. 14, when implant 50 is expanded within a vessel 58, the outwardly-bulging portions of membrane 52 are compressed against the inner walls of vessel 58 to create a plurality of folds/wrinkles in the membrane 52, thereby forming a radial and circumferential seal between the implant 50 and the inner walls of vessel 58.

While not shown in FIGS. 13-14, it is to be understood that the circumferentially-redundant membrane attachment may be employed simultaneously together with the axially-redundant membrane attachment shown and described above with respect to FIGS. 4-8.

While not shown in FIGS. 6-14, it is to be understood that the sealing device may also be used at the outflow end as well as at the inflow end of a tube graft or EVAR device to mitigate endoleak.

In accordance with FIGS. 1-14 described above, various aspects of the present disclosure describe an intravascular device including a frame having an inflow edge, an outflow edge, and a circumferentially complete axial portion that is configured to decrease in axial length upon the radial expansion of the frame from a configuration that is radially compressed to a configuration that is radially expanded, with the radially expanded configuration being associated with the deployed condition of the intravascular device. The intravascular device may also include a layer of biocompatible membrane applied and interconnected to the radially outer surface of the substantially circumferentially-complete axial portion of the frame, with the membrane layer having an axial length that exceeds the axial length of the substantially circumferentially-complete axial portion of the frame when in its expanded configuration.

In some aspects of the present disclosure, the frame and, in particular, the circumferentially-complete axial portion of the frame, includes a lattice.

The circumference of the biocompatible layer may exceed or not exceed the circumference of the frame portion to which it is interconnected.

The biocompatible membrane may be comprised of fabric or polymer material such as PTFE. In some aspects of the present disclosure, the biocompatible membrane is comprised of a cross-linked and processed mammalian tissue, such as porcine or bovine pericardium. The membrane material may be substantially dry, radially compressed, associated to a delivery catheter, sterilized, and pre-packaged with a delivery system prior to use at implantation.

In the example where the intravascular device is a framed tube graft for endovascular exclusion of an aneurysmal defect, the biocompatible membrane layer may be interconnected to the frame at a series of circumferentially-distributed points axially displaced from the outflow edge of the frame and at a series of circumferentially-distributed points approximating the outflow edge of the frame. In some aspects of the present disclosure, the points of interconnection correspond to nodes or crossing points of the frame lattice. However, in other aspects, the intravascular device may have alternative uses, such as, for example, transcatheter valves. In such scenarios, the inflow and outflow polarities of the frame may be reversed from that which is described above with respect to FIGS. 1-14.

When the frame including the circumferentially-complete axial portion is deployed from a radially-compressed to a fully radially-expanded condition, the circumferentially-complete axial portion of the frame predictably shortens axially, moving the various circumferential membrane layer interconnection points axially toward each other. Such axial movement causes the membrane layer between the interconnection points to become redundant and, therefore, to project radially outward to form a circumferentially-oriented pleat. This radially-outward projection of the membrane layer is circumferential and causes the radially-outward projection of the membrane layer to be interposed between the frame and the native tissue seat, thereby allowing at least a portion of the membrane layer to act as a barrier seal to block the passage of blood between the inner surface of the vessel and the outer surface of the implant. In the example of an EVAR device, the configuration described above may act to block endoleak. However, the device may be used for other purposes, such as reducing prosthetic paravalvular leak.

As long as there is axial separation of these two series of circumferential interconnection points, and there is axial shortening of the corresponding circumferentially complete underlying portion of the frame on expansion from the compressed or crimped configuration, then the interconnection points need not lie directly upon an edge of the frame or upon an edge of that circumferentially complete portion configured to predictably shorten. Further, the biocompatible membrane layer need not terminate in either axial extent at the points of interconnection. In at least one embodiment, the tissue layer extends at least to and is interconnected along (1) an outflow axial extent corresponding to the outflow edge of the frame and (2) an inflow axial extent between the inflow and outflow edges of the frame approximating the axially mid portion of the frame.

The above-disclosed features and functions, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

The invention claimed is:

1. A sealing device for use as a vascular implant comprising:
   a frame, the frame having an at least partial expandable axial extent including a plurality of circumferentially distributed members configured to circumferentially separate from each other when expanded from a radially compressed configuration to a radially expanded configuration; and
   a membrane layer coupled to an outer surface of the at least partial expandable axial extent of the frame at a plurality of connection points, the membrane layer having at least a transverse curvilinear extent exceeding an underlying circumferential extent of the frame between connection points at an axial level of at least some of the connection points upon the frame when the frame is in the radially expanded configuration, the transverse curvilinear extent being a portion of the membrane layer included between the at least some of the connection points such that the transverse curvilinear extent does not have underlying frame members.

2. The sealing device of claim 1, wherein the connection points between the frame and the membrane layer are circumferentially regularly spaced.

3. The sealing device of claim 1, wherein the connection points between the frame and the membrane layer are circumferentially irregularly spaced.

4. The sealing device of claim 1, wherein the at least partial expandable axial extent of the frame is formed as a lattice structure.

5. The sealing device of claim 4, wherein the membrane layer is coupled to the lattice structure at a plurality of axially-spaced and circumferentially-distributed connection points.

6. The sealing device of claim 5, wherein the membrane layer is coupled to the lattice structure by a plurality of sutures.

7. The sealing device of claim 1, wherein the connection points of the frame include a plurality of circumferentially-distributed connection points proximate to an inflow edge of the at least partial expandable axial extent of the frame.

8. The sealing device of claim 1, wherein the one or more connection points of the frame include a plurality of circumferentially-distributed connection points proximate to an outflow edge of the at least partial expandable axial extent of the frame.

9. The sealing device of claim 1, wherein:
   the frame includes an inflow edge and an outflow edge relative to axial blood flow within a vessel; and
   at least a portion of the membrane layer between the inflow edge and the outflow edge of the frame projects radially outward relative to the frame when the at least partial axial extent of the frame is in a radially-expanded configuration.

10. The sealing device of claim 1, wherein the membrane layer is formed of at least one of processed mammalian pericardium tissue, a biocompatible fabric, or a polymer material.

11. The sealing device of claim 1, wherein the membrane layer is formed of at least one of porcine or bovine pericardium tissue.

12. The sealing device of claim 1, wherein the membrane layer is formed of a substantially dry tissue.

13. The sealing device of claim 12, wherein the sealing device is in a radially-compressed condition, associated to a delivery system, and provided together with the delivery system in a sterile condition within an internally sterile package.

14. The sealing device of claim 1, wherein the membrane layer extends over an entire axial length of the frame.

15. The sealing device of claim 1, wherein the membrane layer extends over only a portion of an axial length of the frame.

16. The sealing device of claim 9, wherein the membrane layer axially extends beyond at least one of the inflow edge or the outflow edge of the frame.

17. The sealing device of claim 1, wherein the membrane layer extends over an entire circumferential length of the frame.

18. The sealing device of claim 1, wherein the membrane layer extends over only a portion of a circumferential length of the frame.

19. The sealing device of claim 1, wherein at least a portion of the membrane layer projects in a radially outwardly angled direction relative to the frame.

20. The sealing device of claim 1, wherein one or more of the connections at the connection points enforce a radially outwardly angled direction upon the membrane layer adjacent the connection points.

21. The sealing device of claim 1, wherein two or more portions of the membrane layer are connected at connection points independent of the connections to the frame.

22. The sealing device of claim 21, wherein the connection points form one of a linear or curvilinear seam of at least two points.

23. The sealing device of claim 1, wherein the connection points form one of a linear or curvilinear seam of at least two points.

24. The sealing device of claim 1, wherein a radially projecting portion of the membrane layer is configured to contact an inner wall of the vessel to cause an impeding of blood flow over an outer surface of the sealing device.

25. The sealing device of claim 9, wherein the connection points of the frame include one or more circumferentially-distributed connection points proximate to the outflow edge of the axial extent of the frame, one or more circumferentially-distributed connection points proximate to the inflow edge of the axial extent of the frame, and one or more intermediate connection points located axially between the connection points proximate the outflow edge and the connection points proximate the inflow edge.

26. The sealing device of claim 1, wherein the at least partial axial extent of the frame is configured to decrease in axial length when the circumferentially distributed members circumferentially separate from each other.

27. The sealing device of claim 1, wherein the membrane layer is coupled to the outer surface of the at least partial expandable axial extent of the frame at the plurality of connection points to create a fold in the membrane layer at each such connection point, the fold developing an outward bias in a bulge in the membrane formed between the at least some of the connection points when the frame is in the radially expanded configuration.

* * * * *